United States Patent
Lee et al.

(10) Patent No.: US 10,610,555 B2
(45) Date of Patent: Apr. 7, 2020

(54) METHOD FOR ALLEVIATING OSTEOARTHRITIS BY USING COMPOSITE (HL-JOINT 100) OF ACHYRANTHES BIDENTATA, EUCOMMIN ULMOIDES OLIVER AND POMEGRANATE EXTRACTS, WHICH HAS ANTIINFLAMMATORY EFFECT CAUSED BY COX2 AND PGE2 INHIBITION, CARTILAGE PROTECTIVE EFFECT CAUSED BY MMP-2 AND -9 INHIBITION AND CARTILAGE REGENERATION EFFECT CAUSED BY INCREASE IN TYPE II COLLAGEN SYNTHESIS

(71) Applicants: HLSCIENCE CO., LTD., Gyeonggi-do (KR); Hae-Yeon Lee, Gyeonggi-do (KR)

(72) Inventors: Hae-Yeon Lee, Gyeonggi-do (KR); Beom-Rak Choi, Gyeonggi-Do (KR); Hye-Rim Park, Jeollabuk-Do (KR); Seung-Hee Kim, Gyeonggi-do (KR)

(73) Assignees: HLSCIENCE CO., LTD., Gyeonggi-Do (KR); Hae-Yeon Lee, Gyeonggi-Do (KR)

(*) Notice: Subject to any disclaimer, the term of this patent is extended or adjusted under 35 U.S.C. 154(b) by 118 days.

(21) Appl. No.: 15/781,791

(22) PCT Filed: Aug. 4, 2016

(86) PCT No.: PCT/KR2016/008616
§ 371 (c)(1),
(2) Date: Jun. 6, 2018

(87) PCT Pub. No.: WO2017/099327
PCT Pub. Date: Jun. 15, 2017

(65) Prior Publication Data
US 2018/0360895 A1    Dec. 20, 2018

(30) Foreign Application Priority Data

Dec. 9, 2015 (KR) .......................... 10-2015-0175161

(51) Int. Cl.
*A61K 36/00* (2006.01)
*A61K 36/185* (2006.01)
(Continued)

(52) U.S. Cl.
CPC .......... *A61K 36/185* (2013.01); *A61K 31/366* (2013.01); *A61K 31/573* (2013.01);
(Continued)

(58) Field of Classification Search
CPC .................................................. A61K 36/00
See application file for complete search history.

(56) References Cited

U.S. PATENT DOCUMENTS

2011/0262568 A1   10/2011   Byun

FOREIGN PATENT DOCUMENTS

| CN | 103933216 A | 7/2014 |
|----|-------------|--------|
| EP | 2556837 A1  | 2/2013 |

(Continued)

OTHER PUBLICATIONS

English translation by Google Patents of CN 102949648 A.*

(Continued)

*Primary Examiner* — Rosanne Kosson
(74) *Attorney, Agent, or Firm* — Harness, Dickey & Pierce, P.L.C.

(57) ABSTRACT

The present invention relates to a composition for preventing and treating osteoarthritis, which contains a pomegranate concentrate, a eucommia bark extract and an achyranthis radix extract as active ingredients. More specifically, the composite composition of a pomegranate concentrate, a eucommia bark extract and an achyranthis radix extract (Continued)

according to the present invention has a synergistic effect of improving osteoarthritis. In particular, because it can directly protect and regenerate the cartilage and can improve joint stiffness, it can be used in health food, etc.

12 Claims, 9 Drawing Sheets

(51) Int. Cl.

| | | |
|---|---|---|
| A61K 36/21 | (2006.01) | |
| A61K 36/46 | (2006.01) | |
| A61K 31/7032 | (2006.01) | |
| A61K 31/573 | (2006.01) | |
| A61K 31/366 | (2006.01) | |
| A61P 19/02 | (2006.01) | |

(52) U.S. Cl.
CPC .......... *A61K 31/7032* (2013.01); *A61K 36/21* (2013.01); *A61K 36/46* (2013.01); *A61P 19/02* (2018.01); *A61K 2236/19* (2013.01)

(56) References Cited

FOREIGN PATENT DOCUMENTS

| EP | 3165228 A1 | 5/2017 |
|---|---|---|
| JP | H4-360694 A | 12/1992 |
| JP | 2000-247896 A | 9/2000 |
| JP | 2005-047817 A | 2/2005 |
| JP | 2005-089304 A | 4/2005 |
| JP | 2008-104394 A | 5/2008 |
| JP | 2011-231110 A | 11/2011 |
| KR | 10-2011-0023133 A | 3/2011 |
| KR | 10-2013-0089305 A | 8/2013 |
| KR | 10-2015-0120318 A | 10/2015 |

OTHER PUBLICATIONS

English bibliographic information of CN 102949648 A.*
Nippon Menaade Keshohin KK, JP 2005-089304 A, English abstract, 2005.*
Pola Chem. Ind. Inc., JP 2008-104394 A, English abstract, 2008.*
International Search Report from corresponding PCT Application No. PCT/KR2016/008616, dated Nov. 23, 2016, and it's English translation.
Felson, D. T., et al.; "An Update on the Epidemiology of Knee and Hip Osteoarthritis With a View to Prevention", Arthritis & Rheumatism, vol. 41, No. 8., Aug. 1998, pp. 1343-1355. American College of Rheumatology, 1998.
Tamura, T., et al.; "Rhein, an active metabolite of diaceren, suppresses the interleukin-1alpha-induced proteoglycan degradation in cultured rabbit articular chondrocytes.", Jpn J Pharmacol. Jan. 2001;85(1):101-4.
Qin, J., et al.; "Effect of Angelica sinensis Polysaccharides on Osteoarthritis In Vivo and In Vitro: A Possible Mechanism to Promote Proteoglycans Synthesis", Research Article, Hindawi Publishing Corporation, Evidence-Based Complementary and Alternative Medicine, vol. 2013, Article ID 794761, 15 pages, http://dx.doi.org/10.1155/2013/794761.
Choi, K. W., et al.; "The relationship between pain and eating among overweight and obese individuals with osteoarthritis: an ecological momentary study.", Pain Res Manag. Nov.-Dec. 2014;19(6):e159-63. Epub Jun. 9, 2014.
Kim, D. H., et al.; "Establishment of content criteria of marker compounds through the monitoring of Achyranthis Radix collected from Korea and China", Analytical Science & Technology, vol. 25, No. 4, 250-256, 2012, http://dx.doi.org/10.5806/AST.2012.25.4.250.
Kang, M. L., et al.; "Drug delivery systems for intra-articular treatment of osteoarthritis.", Expert Opin Drug Deliv. Feb. 2014;11(2):269-82. doi: 10.1517/17425247.2014.867325. Epub Dec. 6, 2013.
Moore, E. E., et al.; "Fibroblast growth factor-18 stimulates chondrogenesis and cartilage repair in a rat model of injury-induced osteoarthritis." Osteoarthritis Cartilage. Jul. 2005;13(7):623-31.
Sailer, M., et al.; "Quality of life in patients with benign anorectal disorders", BJS / vol. 85, Issue 12, 1998, https://doi.org/10.1046/j.1365-2168.1998.00958.x.
Rezende, M. U., et al.; "Diacerhein versus glucosamine in a rat model of osteoarthritis." Clinics (Sao Paulo). Oct. 2006;61(5):461-6.
Permuy, M., et al.; "Comparison of various SYSADOA for the osteoarthritis treatment: an experimental study in rabbits", BMC Musculoskeletal Disorders (2015) 16:120.
Selfe, T. K., et al.; "Effects of Meditation on Symptoms of Knee Osteoarthritis.", Altern Complement Ther. Jun. 2013;19(3):139-146. Epub Jun. 18, 2013.
Mundlos, S., et al.; "Heritable diseases of the skeleton. Part I: Molecular insights into skeletal development-transcription factors and signaling pathways.", FASEB J. Feb. 1997;11(2):125-32.
Guzman, R.E., et al.; "Mono-iodoacetate-induced histologic changes in subchondral bone and articular cartilage of rat femorotibial joints: an animal model of osteoarthritis.", Toxicol Pathol. Nov.-Dec. 2003;31(6):619-24.
Rai, M. F., et al.; "Inflammatory mediators: tracing links between obesity and osteoarthritis.", Crit Rev Eukaryot Gene Expr. 2011;21(2):131-42.
Patel, N. A., et al.; "Monitoring osteoarthritis in the rat model using optical coherence tomography", IEEE Journals & Magazine, vol. 24 Issue: 2, 2005, pp. 155-159.
Ganey, T., et al.; "Disc chondrocyte transplantation in a canine model: a treatment for degenerated or damaged intervertebral disc.", Spine (Phila Pa 1976). Dec. 1, 2003;28(23):2609-20.
Cunnane, G., et al.; "Collagenase, cathepsin B and cathepsin L gene expression in the synovial membrane of patients with early inflammatory arthritis." Rheumatology (Oxford). Jan. 1999;38(1):34-42.
Nagase H., et al.; "Matrix Metalloproteinases*", The Journal of Biological Chemistry, vol. 274, No. 31, Issue of Jul. 30, pp. 21491-21494, 1999.
Halliwell B., et al.; "Hydrogen peroxide in the human body", FEBS Letters 486 (2000) 10-13.
Soo Young Bang et al., "Achyranthes japonica exhibits anti-inflammatory effect via NF-kB suppression and HO-1 induction in macrophages" Journal of Ethnopharmacology 144 (2012) 109-117.

* cited by examiner

| (1) Preparation process | (2) Process and Ingredients | (3) Change in contents of ingredients (mg/g) | (4) Yield (kg) |
|---|---|---|---|
| Raw materials | Eucommia bark or achyranthis radix | | 30kg |
| Extraction | Solvent (70% ethanol, hot water), raw material:solvent = 3:20, 121 ℃, 6 hr, 0.15 MPa, extraction for 2 times | | 230 |
| Separation | Solid/liquid sepratation | | |
| Filtration | filtaraion, 100mesh | | |
| Concentration | Temperature, time and pressure | 25 brix | |
| Drying | Spray dry (dextrin 1:9) | | |
| Analysis of marker ingredients | | | |
| Preparation of composite | Pomegranate: eucommia bark: achyranthis radix = 5:4:1 | | |
| Eucommia bark composite | Raw material | | |

FIG. 1

METHOD FOR ALLEVIATING OSTEOARTHRITIS BY USING COMPOSITE (HL-JOINT 100) OF ACHYRANTHES BIDENTATA, EUCOMMIN ULMOIDES OLIVER AND POMEGRANATE EXTRACTS, WHICH HAS ANTIINFLAMMATORY EFFECT CAUSED BY COX2 AND PGE2 INHIBITION, CARTILAGE PROTECTIVE EFFECT CAUSED BY MMP-2 AND -9 INHIBITION AND CARTILAGE REGENERATION EFFECT CAUSED BY INCREASE IN TYPE II COLLAGEN SYNTHESIS

CROSS-REFERENCE TO RELATED APPLICATIONS

This application is a national phase application of PCT Application No. PCT/KR2016/008616, filed on Aug. 4, 2016, which claims the benefit and priority to Korean Patent Application No. 10-2015-0175161, filed Dec. 9, 2015. The entire disclosures of the applications identified in this paragraph are incorporated herein by references.

FIELD

The present invention relates to a composition for preventing and treating osteoarthritis. More specifically, it relates to a composition for preventing and treating osteoarthritis, which contains an active ingredient derived from a natural substance capable of directly treating osteoarticular damage through regeneration of damaged articular cartilage beyond alleviating the symptoms of osteoarthritis.

BACKGROUND

Osteoarthritis (OA) is a disease characterized by the loss of proteoglycans (PGs) which are the major component of articular cartilage, which causes articular dysfunction by leading to destruction of the cells and tissues of the articular cartilage [Felson and Zhang, 1998]. It is known that the expression of MMP-3, MMP-9, MMP-13, etc. is increased in osteoarthritis and the increased MMPs aggravate degenerative arthritis by damaging the collagen matrix constituting the cartilage.

At present, nonsteroidal anti-inflammatory drugs (NSAIDs), analgesics, hyaluronic acid (hyaluronan), glucosamine and chondroitin are mainly used for the treatment of osteoarthritis (OA). However, they are effective in alleviating symptoms only rather than curing the disease. In particular, some NSAIDs are even known to aggravate the symptoms of OA by inhibiting the synthesis of proteoglycans in the articular cartilage [Tamura and Ohmori, 2001]. Accordingly, there is an urgent need of an alternative therapy that can protect the articular cartilage itself or can directly treat the damage. In this regard, efforts are being made in various aspects to find osteoarthritis (OA)-improving agents derived from natural substances. Especially, efforts are being made recently to find a new composite composition with a synergistically enhanced effect of improving osteoarthritis (OA) by combining foods or ingredients derived from natural substances [Tamura and Ohmori, 2001; Qin et al., 2013; Na et al., 2014; Nam et al., 2014].

Until now, some functional foods or ingredients are known to provide synergistic effects when combined appropriately [Lee et al., 2008; Choi et al., 2014ab; Choi et al., 2015; Kang et al., 2015]. But, the osteoarthritis-improving effect of a composite composition of a pomegranate concentrate powder, a eucommia bark and an achyranthis radix extract has never been studied.

SUMMARY

Technical Problem

The present invention is directed to providing a composition for preventing or improving osteoarthritis, which contains a natural substance as an active ingredient, and a method for preventing or improving osteoarthritis by administering the composition. Particularly, the present invention aims at developing a composition for improving osteoarthritis, which has an effect of regenerating damaged articular cartilage or directly treating osteoarticular damage beyond alleviating the symptoms of osteoarthritis.

Technical Solution

The present invention provides a composition for preventing or improving osteoarthritis, which contains a pomegranate concentrate, a eucommia bark extract and an achyranthis radix extract as active ingredients, and a method for preparing the same.

More specifically, in an exemplary embodiment, the present invention provides a composition for preventing or improving osteoarthritis, which contains the eucommia bark extract and the achyranthis radix extract at a weight ratio of 2:1-4:1, a method for preventing or improving osteoarthritis by administering the composition or a use of the composition for preventing or improving osteoarthritis.

In another exemplary embodiment, the present invention provides a composition for preventing or improving osteoarthritis, which contains the pomegranate concentrate, the eucommia bark extract and the achyranthis radix extract at a weight ratio of 5:2:1-5:4:1, a method for preventing or improving osteoarthritis by administering the composition or a use of the composition for preventing or improving osteoarthritis.

In another exemplary embodiment, the present invention provides a composition for preventing or improving osteoarthritis wherein the pomegranate concentrate is obtained by treating a pomegranate pulp with a starch-degrading enzyme and then concentrating under heating, a method for preventing or improving osteoarthritis by administering the composition or a use of the composition for preventing or improving osteoarthritis.

In another exemplary embodiment, the present invention provides a composition for preventing or improving osteoarthritis wherein an extraction solvent of the eucommia bark extract or the achyranthis radix extract is water, a $C_1$-$C_4$ alcohol or a mixture thereof, a method for preventing or improving osteoarthritis by administering the composition or a use of the composition for preventing or improving osteoarthritis.

In another exemplary embodiment, the present invention provides a composition for preventing or improving osteoarthritis wherein the pomegranate concentrate contains 0.5-2 mg/g of ellagic acid, a method for preventing or improving osteoarthritis by administering the composition or a use of the composition for preventing or improving osteoarthritis.

In another exemplary embodiment, the present invention provides a composition for preventing or improving osteoarthritis wherein the eucommia bark water extract contains 0.5-3 mg/g of pinoresinol diglucoside, a method for preventing or improving osteoarthritis by administering the composition or a use of the composition for preventing or improving osteoarthritis.

In another exemplary embodiment, the present invention provides a composition for preventing or improving osteoarthritis wherein the eucommia bark alcohol extract contains 0.8-4 mg/g of pinoresinol diglucoside, a method for preventing or improving osteoarthritis by administering the composition or a use of the composition for preventing or improving osteoarthritis.

In another exemplary embodiment, the present invention provides a composition for preventing or improving osteoarthritis wherein the achyranthis radix water extract contains 0.1-0.5 mg/g of ecdysterone, a method for preventing or improving osteoarthritis by administering the composition or a use of the composition for preventing or improving osteoarthritis.

In another exemplary embodiment, the present invention provides a composition for preventing or improving osteoarthritis wherein the achyranthis radix alcohol extract contains 0.2-2.5 mg/g of ecdysterone, a method for preventing or improving osteoarthritis by administering the composition or a use of the composition for preventing or improving osteoarthritis.

In another exemplary embodiment, the present invention provides a composition for preventing or improving osteoarthritis wherein the composition has an effect of protecting cartilage, regenerating cartilage or improving joint stiffness, a method for preventing or improving osteoarthritis by administering the composition or a use of the composition for preventing or improving osteoarthritis.

In another exemplary embodiment, the present invention provides a composition for preventing or improving osteoarthritis wherein the composition is a health functional food composition or a pharmaceutical composition, a method for preventing or improving osteoarthritis by administering the composition or a use of the composition for preventing or improving osteoarthritis.

In another aspect, the present invention provides a method for preparing a composition for preventing and treating osteoarthritis, which contains a pomegranate concentrate, a eucommia bark extract and an achyranthis radix extract as active ingredients, including:

a step of preparing a pomegranate concentrate by adding a starch-degrading enzyme to a pomegranate pulp and concentrating under heating;

a step of preparing a eucommia bark extract by adding water, a $C_1$-$C_4$ lower alcohol or a mixture thereof solvent to eucommia bark;

a step of preparing an achyranthis radix extract by adding water, a $C_1$-$C_4$ lower alcohol or a mixture thereof solvent to achyranthis radix; and a step of mixing and stirring the pomegranate concentrate, the eucommia bark extract and the achyranthis radix extract.

Hereinafter, the present invention is described in detail.

[Pomegranate Concentrate, Eucommia Bark Extract and Achyranthis Radix Extract]

The inventors of the present invention have found out that a composite of a pomegranate concentrate (PCP), a eucommia bark extract (EC) and an achyranthis radix extract (AR) has a synergistic biological activity in preventing and improving osteoarthritis.

Pomegranate (*Punica granatum* L) is a plant native to southwestern Asia, northwestern India and California of the USA and is widely distributed in subtropical and tropical regions at present. From long ago, pomegranate, especially red pomegranate, has been known as a tonic. In particular, it is known to have good effects on prevention of hypertension and arteriosclerosis. It contains water-soluble sugars in large quantities of 38-47% and also contains various vitamins and minerals.

Specifically, the pomegranate used in the present invention may be red pomegranate, although not being specially limited thereto. Specifically, red pomegranate from Iran, California, Taiwan, Uzbekistan, Turkey or Korea may be used. For example, Turkish pomegranate cultivars include Hicaznar pomegranate cv., Cekirdeksiz VI pomegranate cv., Silifke Asisi pomegranate cv., Katirbasi pomegranate cv., Lefan pomegranate cv., etc., although not being limited thereto. The pomegranate extract according to the present invention may vary depending on the region, harvest time, etc. of the pomegranate.

In the present invention, the term "concentrate" includes a concentrate obtained by the method described below and concentrates of all forms that can be obtained from the concentrate, including a diluted solution of the concentrate, a dried product obtained by drying the concentrate, a crude purification product or a purification product of the concentrate, a mixture thereof, etc.

Specifically, pomegranate pulp may be used to prepare the pomegranate concentrate according to the present invention.

The pomegranate concentrate according to the present invention may be prepared as follows. For example, after washing pomegranate, the rind and seeds are completely removed. After sterilizing at high temperature in a short time, polysaccharides such as starch contained in the pomegranate are degraded by adding a starch-degrading enzyme. Then, after optionally controlling the turbidity, color, viscosity, etc. of the pomegranate concentrate by adding an additive such as gelatin, silicon dioxide, bentonite, silica sol, tannin, cellulose, potassium caseinate, etc., the pomegranate concentrate may be prepared by concentrating under heating. In addition, a filtering step may be included in between the respective steps. For example, one or more filtering step may be included between the step of removing the rind and seeds and the step of sterilizing at high temperature, between the step of treating with the starch-degrading enzyme and the concentration step or after the concentration step.

More specifically, the concentrate may be prepared through the following steps:

S1) a step of removing the rind and seeds of pomegranate and obtaining the pomegranate pulp only;

S2) a step of sterilizing the pomegranate pulp at 100-105° C. for 50-80 seconds and then cooling to 48-55° C.;

S3) a step of treating the cooled pomegranate pulp with a starch-degrading enzyme at 48-55° C.; and S4) a step of concentrating the degraded pomegranate pulp under heating sequentially at high temperature and high pressure of 70-100° C. and 400-850 mbar for two or more times and at low temperature and low pressure of 40-80° C. and 100-350 mbar for one or more time.

Optionally, a filtering step may be included between the step S1 and the step S2, between the step S3 and the step S4 or after the step S4.

Hereinafter, each step is described in more detail.

S1) Removing Rind and Seeds of Pomegranate and Obtaining Pomegranate Pulp Only

The present invention provides an extract using only the pomegranate pulp not containing the rind and seeds of pomegranate. The rind and seeds of pomegranate may cause side effects. For example, pomegranate certain alkaloids contained in the rind may negatively affect the body function and poisoning may cause seizure, convulsion, stupor, etc. by affecting the respiratory system and muscles. And, the extract of pomegranate seeds may cause allergic side effects such as tongue swelling in some people.

S2) Sterilizing Pomegranate Pulp at 100-105° C. for 50-80 Seconds and then Cooling to 48-55° C.

The pomegranate pulp is sterilized and then cooled. The sterilization is performed at 100-105° C. for 50-80 seconds, more specifically quickly for 55-70 seconds, and the cooling is performed specifically at 48-55° C.

S3) Treating Cooled Pomegranate Pulp with Starch-Degrading Enzyme at 48-55° C.

The cooled pomegranate pulp is treated with a starch-degrading enzyme. The treatment may be performed specifically at 48-55° C. for 10-60 minutes, more specifically at 48-55° C. for 20-40 minutes. As the starch-degrading enzyme, various starch-degrading enzymes known in the art may be used without particular limitation. For example, pectinase, proteinase, amylase, cellulase, etc. may be used. Specifically, pectinase may be used.

S4) Concentrating Degraded Pomegranate Pulp Under Heating Sequentially at High Temperature and High Pressure of 70-100° C. and 400-850 Mbar for Two or More Times and at Low temperature and low pressure of 40-80° C. and 100-350 mbar for one or more time The degraded pomegranate pulp is concentrated under heating sequentially at high temperature and high pressure and at low temperature and low pressure.

Specifically, it may be concentrated under heating at high temperature and high pressure for two or more times, more specifically three or more times, and may be concentrated under heating at low temperature and low pressure for one or more time, more specifically two or more times, for a total of three or more times.

The concentration under heating at high temperature and high pressure is performed at 70-100° C. and 400-850 mbar. Within the above temperature and pressure ranges, the temperature and pressure may be varied for each run of the concentration under heating without limitation. Specifically, the concentration under heating may be performed firstly at 70-85° C. and 400-550 mbar, secondly at 85-92° C. and 550-750 mbar and thirdly at 92-100° C. and 750-850 mbar. More specifically, the concentration under heating may be performed firstly at 78-82° C. and 450-500 mbar, secondly at 85-90° C. and 600-650 mbar and thirdly at 92-98° C. and 800-850 mbar.

The concentration under heating at low temperature and low pressure is performed at 40-80° C. and 100-350 mbar. Within the above temperature and pressure ranges, the temperature and pressure may be varied for each run of the concentration under heating without limitation. Specifically, the concentration under heating may be performed fourthly at 60-80° C. and 250-350 mbar and fifthly at 40-60° C. and 100-250 mbar. More specifically, the concentration under heating may be performed fourthly at 65-72° C. and 300-330 mbar and fifthly at 45-55° C. and 100-150 mbar.

The pomegranate concentrate according to the present invention contains 0.5-3 mg/g of ellagic acid based on the total weight of the pomegranate concentrate. More specifically, it contains 0.5-2 mg/g of ellagic acid based on the total weight of the pomegranate concentrate. It is thought that the reason why the pomegranate concentrate according to the present invention contains ellagic acid at the high content is because of the difference in region, use of the pulp only, preparation method (e.g., concentration method, heating temperature and pressure), etc. However, the present invention is not limited thereby.

Eucommia bark refers to the stem bark of eucommia tree (Eucommia ulmoides Oliver (family Eucommiaceae)) with the periderm removed. It is board-shaped and the edge portions are somewhat curved inwardly. The length and width are not uniform and the thickness is 3-7 mm. The outer surface is light brown or gray-brown. Some have distinct wrinkle patterns or vertically split patterns and some are relatively thin. Distinct lenticels are observed when the coarse bark is unscraped. The inner surface is smooth and brown or dark brown and has vertical wrinkles. The surface is weak and breaks easily. When it is broken, fine, dense, silvery and elastic rubber threads appear. When the cross section is observed under a microscope, the thick rhytidome is located at the outermost side. Inside the rhytidome, several layers of cork cells are aligned regularly. The cell walls of these cells are lignified and the phelloderm lies therebelow. The phloem takes up most of the area with stone cell rings in a transverse arrangement of 5-7 rows, each ring with 3-5 stone cells. The medullary rays consist of 2-3 rows of cells, located close to the cork layer, sometimes leaning to one side. Parenchyma cells including white gutta-percha can be observed near the pith. These parenchyma cells are particularly abundant inside the phloem.

Achyranthis radix is the root of *Achyranthes japonica* Nakai or *Achyranthes bidentata* Blume (family Amaranthaceae). It is a cylindrical main root with numerous lateral roots, 5-20 cm in length and 3-5 mm in diameter, with short remains of the rhizome at the top. The external surface is grayish yellow to pale yellow. The texture is hard and brittle and the fractured surface is horn-like, yellowish white to yellowish brown.

In the present invention, the term "extract" includes an extract obtained from extraction and extracts of all forms that can be obtained from the extract, including a diluted or concentrated solution of the extract, a dried product obtained by drying the extract, a crude purification product or a purification product of the extract, a mixture thereof, etc.

Within a range not negatively affecting the purpose of the present invention, the extract according to the present invention may contain, in addition to the specified part of each plant, its leaf, stem, bark, root, flower, flower bud, fruit, seed, sap and whole plant.

The extract according to the present invention may be prepared by those of ordinary skill using any appropriate method known in the art. For example, it may be prepared by solvent extraction. A solvent extract may be obtained by pulverizing the whole plant or any part of it (e.g., using a blender) and then treating with an extraction solvent. A drying process may precede the pulverization. Also, the solvent extract may be prepared into a powder through an addition process such as distillation under reduced pressure, freeze-drying, spray drying, etc.

The extraction solvent is not particularly limited any solvent known in the art may be used. Non-limiting examples of the extraction solvent include: water; a $C_1$-$C_4$ lower alcohol such as methanol, ethanol, propyl alcohol, butyl alcohol, etc.; a polyhydric alcohol such as glycerin, butylene glycol, propylene glycol, etc.; a hydrocarbon-based solvent such as methyl acetate, ethyl acetate, acetone, benzene, hexane, diethyl ether, dichloromethane, etc.; or a mixture thereof. Specifically, water or a lower alcohol may be used either alone or in combination. A solvent extract may be prepared by conducting extraction one or more times using the solvent and the solvent extract may be prepared into a dried extract by conducting distillation under reduced pressure and then freeze-drying or spray-drying the same.

The amount of the extraction solvent may vary depending on the extraction solvent used. For example, it may be used in an amount of 1-20 times or 5-20 times, more specifically 5-10 times, most specifically 5-8 times, based on the dry weight of the corresponding plant.

The solvent extraction may be performed at a 100-150° C. and 0.1-0.3 MPa for 5-10 hours, although not being limited thereto.

In addition, various extraction processes known in the art, e.g., maceration, infusion, percolation, digestion, decoction, hot continuous extraction, aqueous-alcoholic extraction, countercurrent extraction, microwave-assisted extraction, ultrasonic extraction, supercritical fluid extraction, phytonic extraction (e.g., using a hydrofluorocarbon solvent), etc. may be used either alone or in combination.

The eucommia bark extract according to the present invention contains pinoresinol diglucoside. Particularly, the eucommia bark water extract contains 0.5-3 mg/g of pinoresinol diglucoside based on the total weight of the eucommia bark water extract and the eucommia bark alcohol extract contains 0.8-4 mg/g of pinoresinol diglucoside based on the total weight of the eucommia bark alcohol extract. It is thought that the reason why the eucommia bark extract according to the present invention contains pinoresinol diglucoside of the above-described concentration is because of the difference in region, used part, preparation method (e.g., extraction solvent), etc. However, the present invention is not limited thereby.

The achyranthis radix extract according to the present invention contains ecdysterone. Particularly, the achyranthis radix water extract contains 0.1-0.5 mg/g of ecdysterone based on the total weight of the achyranthis radix water extract and the achyranthis radix alcohol extract contains 0.2-2.5 mg/g of ecdysterone based on the total weight of the achyranthis radix alcohol extract. It is thought that the reason why the achyranthis radix extract according to the present invention contains ecdysterone of the above-described concentration is because of the difference in region, used part, preparation method (e.g., extraction solvent), etc. However, the present invention is not limited thereby.

[Compositions]

The present invention provides a composition for use in preventing or improving osteoarthritis. More specifically, the present invention provides a composition for use in preventing or improving osteoarthritis, which contains a pomegranate concentrate, an achyranthis radix extract and a eucommia bark extract as active ingredients.

The composition according to the present invention contains a pomegranate concentrate, an achyranthis radix extract and a eucommia bark extract as active ingredients.

In the present invention, "contains as an active ingredient" means addition in an amount capable of exhibiting the effect of improving or treating osteoarthritis with the composition according to the present invention. In addition, various adjuvant ingredients for delivery to target cells, stabilization, etc. may be added for formulation into various forms.

In the composition according to the present invention, the respective ingredients may be contained at the following ratios.

A weight ratio of the eucommia bark extract and the achyranthis radix extract may be 2:1-4:1. A superior synergistic effect is achieved within the above weight ratio range.

Or, a weight ratio of the pomegranate concentrate, the eucommia bark extract and the achyranthis radix extract may be 5:2:1-5:4:1. The most superior synergistic effect is achieved within the above weight ratio range.

In addition, each extract (and concentrate) of the composition according to the present invention may be contained in the final composition within a range of about 0.0001-90%, 0.001-90%, 0.01-90%, 0.1-90%, 0.1-90%, 0.1-80%, 0.1-70%, 0.1-60%, 0.1-50%, 0.1-40%, 0.1-30%, 0.1-20% or 0.1-10%.

Also, the composition according to the present invention may contain the complex of the present invention within a range of about 0.0001%, 0.001%, 0.01%, 0.1%, 1%, 5%, 10%, 15%, 20%, 25%, 30%, 35%, 40%, 45%, 50%, 60%, 65%, 70%, 75%, 80%, 85%, 90% or 99% or higher The % may be calculated as weight based on the total weight or volume based on the total volume of the composition and the concentration may be controlled depending on the desired effect of the composition or the product in which the composition is used.

The composition according to the present invention may be prepared by mixing a pomegranate concentrate, a eucommia bark extract and an achyranthis radix extract. In addition, an additional process may be introduced to improve the storage, distribution and stability properties of the composition.

The composition according to the present invention may be prepared into various products. For example, it may be prepared into a food composition, a pharmaceutical composition, etc.

The present invention provides a pharmaceutical composition containing one of the compositions described above. The present invention provides a method for preventing, improving or treating osteoarthritis by administering one of the compositions described above.

The pharmaceutical composition according to the present invention may contain a pharmaceutically effective amount of the pomegranate concentrate, the achyranthis radix extract and the eucommia bark extract alone and may further contain one or more pharmaceutically acceptable carrier, excipient or diluent.

The term "pharmaceutically acceptable" means a non-toxic composition which is physiologically acceptable and, when administered to a human, generally does not cause allergic reactions such as gastrointestinal disorder and dizziness or reactions similar thereto while not negatively affecting the action of the active ingredients.

Examples of the carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, mineral oil, etc. In addition, the pharmaceutical composition may further contain a filler, an anticoagulant, a lubricant, a wetting agent, a fragrance, an emulsifier, an antiseptic, etc.

The "pharmaceutically effective amount" refers to an amount exhibiting a desired effect as compared to a negative control group, specifically an amount sufficient to improve, prevent and/or treat osteoarthritis.

In addition, the pharmaceutical composition of the present invention may be prepared into a formulation that can provide fast, continued or delayed release of the active ingredient after being administered to a mammal using the method known in the art. The formulation may be a powder, a granule, a tablet, an emulsion, a syrup, an aerosol, a soft or hard gelatin capsule, a sterile injection solution or a sterilized powder.

The pharmaceutical composition of the present invention may be administered orally or parenterally although the administration route is not limited thereto. Examples of parenteral administration routes may include transdermal, intranasal, intraabdominal, intramuscular, subcutaneous or intravenous routes. For oral administration, the composition may be formulated as a tablet, a capsule, a cachet, a gelcap, a solution, a suspension, etc. The tablet or capsule may be prepared by a commonly employed method together with a pharmaceutically acceptable excipient such as a binder (e.g., pregelatinized cornstarch, polyvinylpyrrolidone or hydropxypropyl methyl cellulose), a filler (e.g., lactose, microcrystalline cellulose or calcium hydrogen phosphate), a lubricant (e.g., magnesium stearate, talc or silica), a disintegrant (e.g., potato starch or sodium starch glycolate) or a wetting agent (e.g., sodium lauryl sulfate). The tablet may be coated according to a method well known in the art. A liquid formulation for oral administration may be a solution, a syrup or a suspension, although not being limited thereto. Before being used, it may exist as an anhydrous form to be mixed with water or another suitable vehicle. The liquid formulation may be prepared by a commonly employed method using a pharmaceutically acceptable additive such as a suspending agent (e.g., sorbitol syrup, cellulose derivative or hydrogenated edible fat), an emulsifier (e.g., lecithin or acacia gum), a nonaqueous vehicle (e.g., almond oil, oily ester, ethyl alcohol or fractionated vegetable oil) or an antiseptic (e.g., methyl or propyl p-hydroxybenzoate or sorbic acid). The formulation may contain a buffering salt, a flavor, a colorant or a sweetener as occasion demands. The formulation for oral administration may be prepared to provide slow, controlled or continued release of the active ingredient to treat osteoarthritis.

A preferred administration dosage of the composition of the present invention may be adequately determined by those skilled in the art although it varies depending on the condition and body weight of a patient, degree of a disease, composition type, administration route and administration period.

The composition of the present invention may be used either alone or in combination with surgery, radiation therapy, hormone therapy, chemotherapy or a method using a biological response modifier. For example, the pharmaceutical composition of the present invention may be administered or in combination with a compound known to have an effect of improving, preventing and/or treating osteoarthritis.

The present invention provides a food composition containing one of the compositions described above. The present invention also provides a method for preventing or improving osteoarthritis by administering the composition.

The food composition according to the present invention may contain a sitologically effective amount of a pomegranate concentrate, an achyranthis radix extract and a eucommia bark extract alone or may further contain one or more sitologically acceptable carrier, excipient or diluent.

The food composition of the present invention includes all types of processed natural substances, including a food, a functional food, a nutritional supplement, a health food, a food additive, etc. The food composition may be prepared into various forms according to common methods known in the art.

The type of food is not particularly limited. Examples of the food to which the active ingredient can be added include a drink, a meat, a sausage, a bread, a biscuit, a rice cake, a chocolate, a candy, a snack, a cookie, a pizza, an instant noodle, other noodles, a gum, a dairy product including ice cream, a soup, a beverage, an alcohol beverage, a vitamin complex, a milk product, a processed milk product and common health foods.

The complex of the pomegranate concentrate, the achyranthis radix extract and the eucommia bark extract according to the present invention may be added to a food either alone or in combination with another food or a food ingredient and may be used adequately according to a common method. The mixing amount of the active ingredient may be determined appropriately depending on the purpose of use (for prevention or improvement). Generally, the amount of the complex in a health food may be 0.1-90 wt % based on the total weight of the food. However, the amount may be smaller when it is ingested for a long period of time for the purpose of health or hygiene. In addition, the active ingredient may be used in a larger amount than the above-described range because it has no safety problem.

The food composition of the present invention may contain, in addition to the complex of the pomegranate concentrate, the achyranthis radix extract and the eucommia bark extract of the specified ratio as an essential ingredient, other ingredients without particular limitation and may further contain various flavors, natural carbohydrates, etc. commonly used in drinks. Examples of the natural carbohydrate include a sugar such as a monosaccharide, e.g., glucose, fructose, etc., a disaccharide, e.g., maltose, sucrose, etc. and a polysaccharide, e.g., dextrin, cyclodextrin, etc. and a sugar alcohol such as xylitol, sorbitol, erythritol, etc. In addition, a natural flavor (thaumatin or stevia extract (e.g., rebaudioside A, glycyrrhizin, etc.)) or a synthetic flavor (saccharin, aspartame, etc.) may be advantageously used as a flavor.

In addition, the food composition of the present invention may contain various nutrients, vitamins, minerals (electrolytes), flavors such as synthetic flavors and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated beverages, etc. In addition, it may contain a pulp for preparing a natural fruit juice, a fruit juice drink or a vegetable drink.

The composition according to the present invention may be provided as a kit.

The composition according to the present invention is contained in a container. The container may include a bottle, a metal tube, a laminate tube, a plastic tube, a dispenser, a pressurized container, a barrier container, a package, a compartment, a compact container, a pan that can hold a composition, or other types of containers such as a plastic container injection- or blow-molded into a bottle, dispenser or package in which a dispersion medium or a composition is retained, although not being limited thereto. The kit may contain an instruction about the use of the kit or the composition. The instruction may be described in a separate paper or may be described on the surface of the container or on the surface of a packaging material of the container. The instruction may include a word, a phrase, an abbreviation, a picture, a symbol, etc., although not being limited thereto. For example, the instruction may include instructions about how to use, apply or maintain the kit or the composition. The container may contain a predetermined amount of the composition.

[Improvement, Prevention and/or Treatment of Osteoarthritis]

The composition according to the present invention is effective in improving, preventing and/or treating osteoarthritis.

More specifically, the composition according to the present invention has an effect of alleviating and improving the symptoms of osteoarthritis and, furthermore, regenerating damaged articular cartilage or directly treating osteoarticular damage.

More specifically, the composite composition according to the present invention exhibits an effect of preventing osteoarthritis through inhibition of COX-2 and PGE2, protecting cartilage through inhibition of MMP-2 and -9 and regenerating cartilage through increased synthesis of collagen type II.

More specifically, the composite composition according to the present invention is effective in decreasing knee joint thickness (FIG. 6), decreasing PGE2 content the in femoral articular cartilage (FIG. 7), decreasing the number of COX-2-immunopositive cells in the femoral articular cartilage (FIG. 8a) and decreasing the number of TNF-$\alpha$-immunopositive cells in the femoral articular cartilage (FIG. 8b). Especially, the groups administered with composite compositions of PCP (pomegranate concentrate) and EC (eucommia bark extract):AR (achyranthis radix extract) (4:1, 2:1) showed excellent effect as compared to the groups administered with single formulas or composite compositions of other ratios. In addition, the groups administered with the composite composition according to the present invention showed significant decrease in joint stretching angle and epithelial thickness of the joint capsule. A joint stiffness-inhibiting effect similar to that of the diclofenac-administered group was observed in rats with surgically-induced osteoarthritis (OA) (FIG. 9). Also, the groups administered with the composite compositions of PCP and EC:AR (4:1, 2:1) showed a significant effect of inhibiting the decrease of the expression of mRNAs involved in chondrogenesis as compared to the groups administered with PCP, EC or AR alone or composite compositions of other ratios. The group orally administered with the composite composition of PCP and EC:AR (4:1) showed an effect inhibiting the change in the expression of mRNAs involved in chondrogenesis in rats with surgically-induced osteoarthritis (OA) similar to that of the group subcutaneously administered with diclofenac. Also, composite compositions of PCP and EC:AR at adequate ratios synergistically enhanced the formation of cartilage extracellular matrix and inhibited fibrosis in the joint capsule through anti-inflammation and protection and promoted proliferation of cartilage cells. Among them, the composite composition of PCP and EC:AR (4:1) showed the most superior effect of promoting the formation of the cartilage extracellular matrix. In addition, the groups administered with the composite compositions of PCP and EC:AR (4:1, 2:1) showed significantly increased collagen type II mRNA expression in the femoral and tibial articular cartilage as compared to the groups administered with PCP, EC or AR alone or composite compositions of other ratios (Table 3). Also, the groups administered with the composite compositions of PCP and EC:AR (4:1, 2:1, 1:1) showed significantly increased femoral articular cartilage thickness as compared to the groups administered with PCP, EC or AR alone or composite compositions of other ratios. Among them, the composite composition of PCP and EC:AR (4:1) showed the most superior effect of protecting the articular cartilage (FIG. 10). In addition, the groups administered with the composite compositions of PCP and EC:AR (4:1, 2:1) showed significantly increased number of BrdU-immunopositive cells in the femoral and tibial articular cartilage and decreased number of BrdU-immunopositive cells in the joint capsule as compared to the groups administered with PCP, EC or AR alone or composite compositions of other ratios. The composite composition of PCP and EC:AR (4:1) showed the most superior effect of promoting the proliferation of articular cartilage cells (FIG. 11). In addition, the composite compositions of PCP and EC:AR (4:1, 2:1) synergistically enhance the effect of protecting cartilage cells through inhibition of MMP activity by PCP, EC and AR. Of the two, the composite composition of PCP and EC:AR (4:1) showed the most superior effect of inhibiting the activity of MMP-2 and MMP-9. The oral administration of the composite composition of PCP and EC:AR (4:1) showed an effect of inhibiting the activity of MMP-2 and MMP-9 in rats with surgically-induced osteoarthritis (OA) similar to that of the group subcutaneously administered with diclofenac (FIG. 12).

The composite composition of the pomegranate concentrate (PCP), the eucommia bark extract (EC) and the achyranthis radix extract (AR) has a superior effect of improving osteoarthritis, etc. as compared to the single compositions alone due to a synergistic action. In particular, a remarkably superior effect of improving osteoarthritis, etc. is exerted when the weight ratio of the eucommia bark extract and the achyranthis radix extract is 2:1-4:1 and, more specifically, when the weight ratio of the pomegranate concentrate, the eucommia bark extract and the achyranthis radix extract is 5:2:1-5:4:1.

Advantageous Effects

The composition according to the present invention is safe for the human body because it contains natural substances as active ingredients. Especially, it has an effect of regenerating damaged articular cartilage or directly treating osteoarticular damage beyond alleviating the symptoms of osteoarthritis. Accordingly, it can be usefully used as a composition for preventing or improving osteoarthritis in various applications (health food, medicine, etc.)

BRIEF DESCRIPTION OF THE DRAWINGS

The accompanying drawings illustrate a preferred embodiment of the present invention and together with the foregoing disclosure, serve to provide further understanding of the technical features of the present invention, and thus, the present invention is not construed as being limited to the drawings.

FIG. 1 schematically describes preparation of a composite composition according to an exemplary embodiment of the present invention.

EXAMPLES

Figure 2:
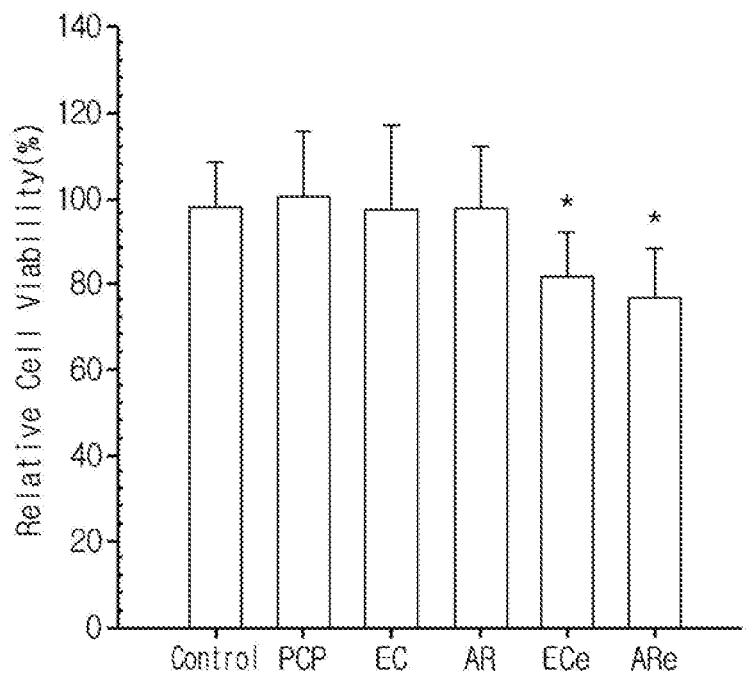
FIG. 2 shows the cell viability of articular cartilage cells treated with a pomegranate concentrate powder (PCP), a eucommia bark water extract powder (EC), an achyranthis radix water extract powder (AR), a eucommia bark ethanol extract powder (ECe) and an achyranthis radix ethanol extract powder (ARe) (The values are mean±SD for 6 experiments. * indicates $p<0.05$ with respect to a control group in the LSD test.).

Hereinafter, examples of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just examples for the purpose of illustrations only, not intended to limit the scope of the invention, so it should be understood that other equivalents and modifications can be made thereto without departing from the scope of the invention.

1. Preparation of Test Substances

Pomegranate, eucommia bark and achyranthis radix extracts were prepared as described below. For each raw material, two or more lots were prepared under the described extraction conditions and extraction yield, contents of ingredients, properties, etc. were analyzed.

1.1 Preparation of Pomegranate Concentrate Powder

A pomegranate concentrate was prepared as follows.

First, 1000 kg of pomegranate were washed after removing foreign materials and sorting out damaged fruits. The separated fruits were cut and the rind and seeds were removed to obtain 450 kg of a pomegranate pulp. After filtration, the pomegranate pulp was sterilized at 100-105° C. for 60 seconds and then cooled to 48-55° C. By adding pectinase 70-100 mL per 1000 L of the resulting pomegranate juice, starches were degraded at 48-55° C. for 30 minutes. Then, after adding 900 g of bentonite per 10000 L of the pomegranate juice to maintain turbidity and color and provide viscosity favorable for drinking, the mixture was stirred at 48-55° C. for 10 minutes. Then, after filtering through 1.5-mm and 1-mm filters under reduced pressure, the mixture was concentrated under heating (sequentially, at 80° C. and 475 mbar to 12 Brix, at 87° C. and 626 mbar to 17 Brix, at 95° C. and 847 mbar to 31 Brix, at 70° C. and 312 mbar to 43 Brix, and at 49° C. and 118 mbar to 65 Brix). Then, a pomegranate concentrate containing 1.8-3.0 mg/g of ellagic acid was obtained by filtering the mixture through a 0.15-mm filter. Finally, a concentrated pomegranate powder containing 0.5-2 mg/g of ellagic acid was prepared by mixing the pomegranate concentrate with dextrin at a ratio of 9:1 and then spray-drying the same.

1.2 Preparation of Eucommia Bark and Achyranthis Radix Extracts (FIG. 1)

For preparation of a eucommia bark and an achyranthis radix extract, dried (roasted) eucommia bark and dried achyranthis radix were purchased from The One Herb (Seoul, Korea). 30 kg of the eucommia bark and achyranthis radix were weighed exactly, washed cleanly and then extracted in an extractor with a raw material:solvent ratio of 3:20 (kg:kg) at 121° C. and 0.15 MPa for 6 hours. This procedure was repeated 2 times. As the solvent, water or 70% ethanol (ethanol or spirit alcohol) was used. After removing solid contents by filtering the extract, the filtrate was concentrated under reduced pressure to obtain a concentrate of 25 Brix (±5 Brix). The concentrate was prepared into a powder through spray drying after mixing with a concentrate:dextrin ratio of 9:1 (kg:kg). Each powdered extract was subjected to ingredient analysis for standardization of raw material and preparation process and safety and efficacy were evaluated through in-vivo and in-vitro experiments.

1.3 Investigation of Contents of Marker Ingredients

The marker ingredients of the pomegranate concentrate powder, the eucommia bark extract powder and the achyranthis radix extract powder were analyzed.

'Ellagic acid' was selected as the marker ingredient of the pomegranate concentrate powder. 'Pinoresinol diglucoside' was selected as the marker ingredient of the eucommia bark extract powder. And, 'ecdysterone' was selected as the marker ingredient of the achyranthis radix extract powder. The result of analyzing the contents of the marker ingredients of the extract powders is summarized in Table 1.

More specifically, the content of the marker ingredient in each extract powder was analyzed as follows.

The ellagic acid content in the pomegranate concentrate powder was quantified as follows.

For preparation of a standard solution, an adequate amount of a standard substance was dissolved in methanol to 1.0 mg/mL. The solution was agitated and diluted with methanol to obtain a standard solution (e.g., 5-200 mg/L). For preparation of a test solution, about 0.5 g of the pomegranate concentrate powder was precisely weighed and dissolved in 10 mL of an extraction solvent (ethanol:distilled water:hydrochloric acid=10:60:8) in a 50-mL volumetric flask. After covering the flask with a lid, the mixture was hydrolyzed and extracted at 90° C. for 1 hour in a water bath. After cooling completely to room temperature and making the volume 20 mL by adding methanol, the mixture was filtered through a 0.45-μm PTFE membrane filter to obtain a test solution.

For chromatography, a UV absorption detector (measurement wavelength 370 nm) and a stainless steel column with an inner diameter of 4-6 mm and a length 15-25 cm, packed with 5-10 μm of octadecyl silica gel for liquid chromatography, was used. The column temperature was set constant around 40° C. and the concentration gradient was controlled in a stepwise manner with a mobile phase A and a mobile phase B (mobile phase A=85% phosphoric acid:methanol=6:4, mobile phase B=methanol).

Ellagic acid content (mg/g)={calibration curve concentration (m/mL)×total test solution volume (mL)×purity of standard substance}/{sample volume (α)×100}.

The eucommia bark extract powder was quantitatively analyzed according to the Korean Herbal Pharmacopoeia.

After precisely weighing about 1.0 g of the eucommia bark extract powder and adding 20 mL of diluted ethanol (75→100), the mixture was ultrasonically extracted for 30 minutes and then filtered to prepare a test solution. Separately from this, about 10 mg of standard pinoresinol diglucoside was precisely weighed and then dissolved in diluted ethanol (75→100) to make 100 mL. 10 mL of the solution was taken accurately and diluted ethanol (75→100) was added to make 50 mL accurately to be used as a standard solution. 10 μL of each of the test solution and the standard solution was subjected to liquid chromatography to measure the peak areas AT and AS of the test solution and the standard solution.

Quantity of pinoresinol diglucoside ($C_{32}H_{42}O_{16}$) (mg)=quantity of standard pinoresinol diglucoside (mg)×Aγ/Aδ×1/25

For chromatography, a UV absorption detector (measurement wavelength 230 nm) and a stainless steel column with an inner diameter of 4-6 mm and a length 15-25 cm, packed with 5-10 μm of octadecyl silica gel for liquid chromatography, was used. The column temperature was set constant around 35° C. and the concentration gradient was controlled in a stepwise manner with a mobile phase A and a mobile phase B (mobile phase A=diluted formic acid (1→1000), mobile phase B=acetonitrile).

The achyranthis radix extract powder was quantitatively analyzed using ecdysterone as a marker ingredient according to the method of Kim et al. (*Analytical Science & Technology*. 25(4), 250-256, 2012). Details are as follows.

The sample was prepared into a powder and transferred to a 50-mL test tube with a stopper. Then, 20 mL of 50% ethanol was added. The test tube was mounted on an ultrasonic extractor. After conducting extraction at room temperature for 90 minutes, centrifugation was performed at 3,000 rpm for 5 minutes. 500 μL of the supernatant was taken and, after adding 100 μL of 350 ppm syringic acid as an internal standard, filtered through a 0.22-μm membrane filter to obtain a test solution. As a standard solution for constructing a calibration curve, standard ecdysterone was dissolved in methanol to prepare a 1 mg/mL stock solution and then serially diluted. Chromatography was conducted as follows. As a mobile phase, a mixture of 0.08% formic acid and acetonitrile (85:15, v/v) was flown at a rate of 1 mL/min. The injection volume was 30 μL and detection was made at UV 254 nm. The column temperature was set to 30° C. According to the ICH guideline, the linearity of the calibration curve of the marker ingredient of the achyranthis radix was investigated and within-run precision and between-day precision were determined through repeated experiments. In addition, accuracy, selectivity, quantitation range and yield were determined. The isolated ingredients were identified by LC/MS in the positive ion mode with a gas flow rate of 50 L/min, an ion source temperature of 600° C. and a detector voltage of 2.0 kV.

TABLE 1

| Sample | Content of marker ingredient (mg/g) | Mean |
|---|---|---|
| Eucommia bark hot water extract 1 | 1.66 | 1.62 ± 0.05 |
| Eucommia bark hot water extract 2 | 1.58 | |
| Eucommia ethanol (spirit alcohol) extract 1 | 2.59 | 2..11 ± 0.67 |
| Eucommia ethanol (spirit alcohol) extract 2 | 1.63 | |
| Achyranthis radix hot water extract 1 | 0.25 | 0.25 ± 0.007 |
| Achyranthis radix hot water extract 2 | 0.26 | |
| Achyranthis radix ethanol (spirit alcohol) extract 1 | 1.06 | 1.06 |
| Achyranthis radix water ethanol (spirit alcohol) 2 | 1.06 | |
| Pomegranate concentrate powder 1 | 1.2 | 1.17 ± 0.03 |
| Pomegranate concentrate powder 2 | 1.15 | |

2. Evaluation of Efficacy of Single and Mixed Formulas of Pomegranate Concentrate Powder, Eucommia Bark Extract and Achyranthis Radix Extract The anti-inflammatory effect and cartilage-regenerating effect of the single or mixed formula of the pomegranate concentrate powder prepared in 1.1 and the eucommia bark extract and the achyranthis radix extract prepared in 1.2 for an osteoarthritis model were investigated.

2.1 Evaluation of Efficacy Through Cell Experiments

For cartilage sampling, 4- to 6-week-old male SD rats weighing about 180-200 g were cervically dislocated. After disinfecting and cutting open the skin, about 2-3 mm of the articular cartilage was taken and the cartilage cells were cultured. The cultured cartilage cells were treated with the eucommia bark and achyranthis radix extracts and cytotoxicity was investigated by MTT assay.

When the articular cartilage cells isolated from the SD rat were cultured with 10 mg/mL of the pomegranate concentrate powder and the eucommia bark and achyranthis radix water extracts for 24 hours, no significant cytotoxicity was acknowledged as compared to the control group. In contrast, the groups treated with 10 mg/mL of the eucommia bark and achyranthis radix ethanol extracts showed significant ($p<0.05$) decrease in cell viability as compared to the control group (FIG. 2).

In order to investigate the expression of the inflammatory mediator prostaglandin E2 (PGE2), the cultured cartilage cells were treated with the pomegranate, eucommia bark and achyranthis radix extracts and then with 50 μg/mL lipopolysaccaride (LPS). After incubation for 24 hours, the supernatant was isolated and PGE2 was measured. In addition, for measurement of 5-lipoxygenase (5-LO) inhibitory activity, the cartilage cells isolated from the experimental animal were added to a 96-well plate, at a concentration of $1\times10^4$ cells/well, containing a DMEM medium supplemented with 10% FBS. After stabilization for 12 hours, followed by treatment with the test substance at different concentrations and then with LPS, the cells were incubated for 24 hours. Then, the supernatant was isolated and 5-LO was measured.

Figure 3A:
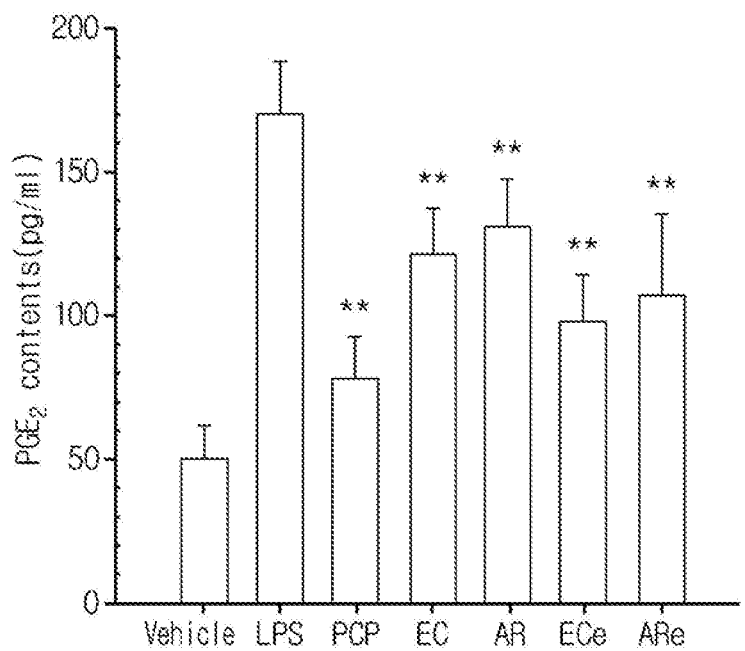
FIG. 3a shows the change in PGE2 content in cartilage cells treated with a pomegranate concentrate powder (PCP), a eucommia bark water extract powder (EC), an achyranthis radix water extract powder (AR), a eucommia bark ethanol extract powder (ECe) and an achyranthis radix ethanol extract powder (ARe).
Figure 3B:
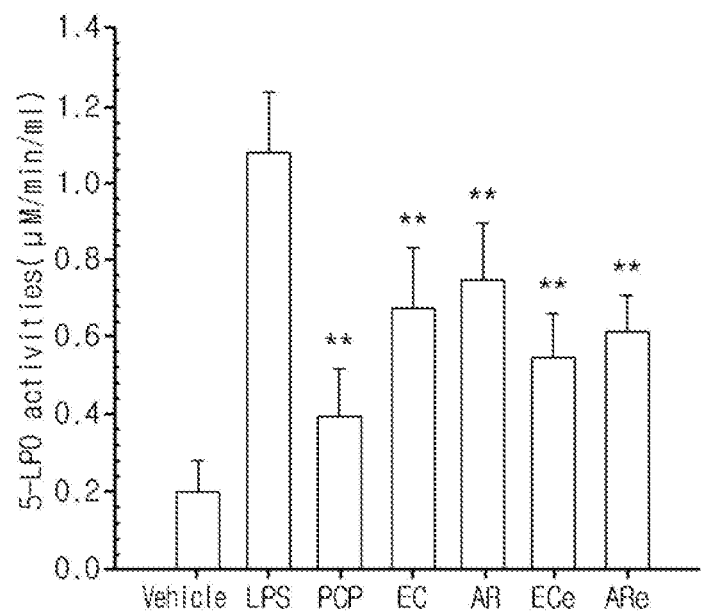
FIG. 3b shows the change in 5-LPO content in cartilage cells treated with a pomegranate concentrate powder (PCP), a eucommia bark water extract powder (EC), an achyranthis radix water extract powder (AR), a eucommia bark ethanol extract powder (ECe) and an achyranthis radix ethanol extract powder (ARe) (The values are mean±SD for 6 experiments. ** indicates $p<0.01$ with respect to a rhIL-1$\alpha$-treated group in the LSD test.).

The anti-inflammatory effect of the test substances was compared by measuring the content of the inflammatory mediator PGE2 and the activity of 5-LPO which is an enzyme critical in the biosynthesis of leukotrienes. When the articular cartilage cells isolated from the SD rat were treated with 50 μg/mL LPS, the PGE2 and 5-LPO contents were significantly ($p<0.01$) increased as compared to the control group. The pomegranate concentrate powder, the eucommia bark ethanol extract, the achyranthis radix ethanol extract, the eucommia bark water extract and the achyranthis radix water extract showed significantly ($p<0.01$) decreased PGE2 and 5-LPO contents as compared to the LPS control group in that order (FIG. 3).

In the inflammatory joint, protein-degrading enzymes such as matrix metalloproteinase (MMP) play an important role in cartilage and bone destruction. MMP is inhibited by the antagonistic system in tissues. In addition, because MMP acts as an extracellular matrix protein in vivo and is involved in the degradation of PG in osteoarthritis, the regulation of MMP activity is known to be very important in the treatment of arthritis.

For the measurement of the activity of matrix metalloproteinase (MMP)-2 and -9 as cartilage resorption markers, the cartilage cells were treated with the test substances of different concentrations and then with rhIL-1a. After incubation for 24 hours, the activity of MMP-2 and -9 was measured from the supernatant.

Figure 4A:
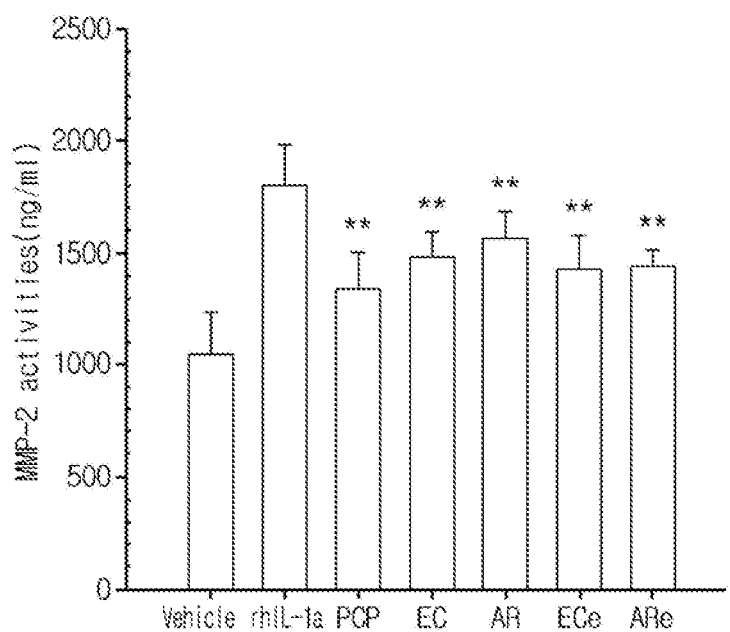
FIGS. 4a and 4b show the effect of inhibiting the activity of MMP-2 (FIG. 4a) and MMP-9 (FIG. 4b) depending on treatment with a pomegranate concentrate powder (PCP), a eucommia bark water extract powder (EC), an achyranthis radix water extract powder (AR), a eucommia bark ethanol extract powder (ECe) and an achyranthis radix ethanol extract powder (ARe) (The values are mean±SD for 6 experiments. ** indicates p<0.01 with respect to a rhIL-1α-treated group in the LSD test.).
Figure 4B:
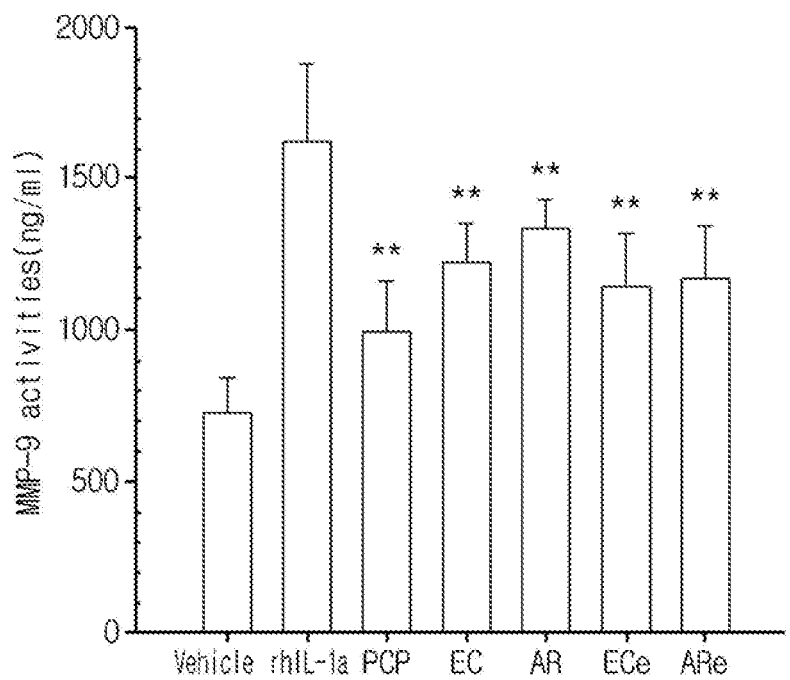

It was found out that the activity of MMP-2 and MMP-9 in the articular cartilage cells isolated from the SD rat was remarkably increased by rhIL-1α. The increased activity of MMP-2 and MMP-9 was remarkably decreased by the pomegranate concentrate powder, the eucommia bark ethanol extract, the achyranthis radix ethanol extract, the eucommia bark water extract and the achyranthis radix water extract in that order. Based on this result, it is thought that the test substances will be effective in inhibiting the destruction of cartilage tissue by inhibiting the activity of MMP-2 and MMP-9 (FIG. 4).

Figure 5:
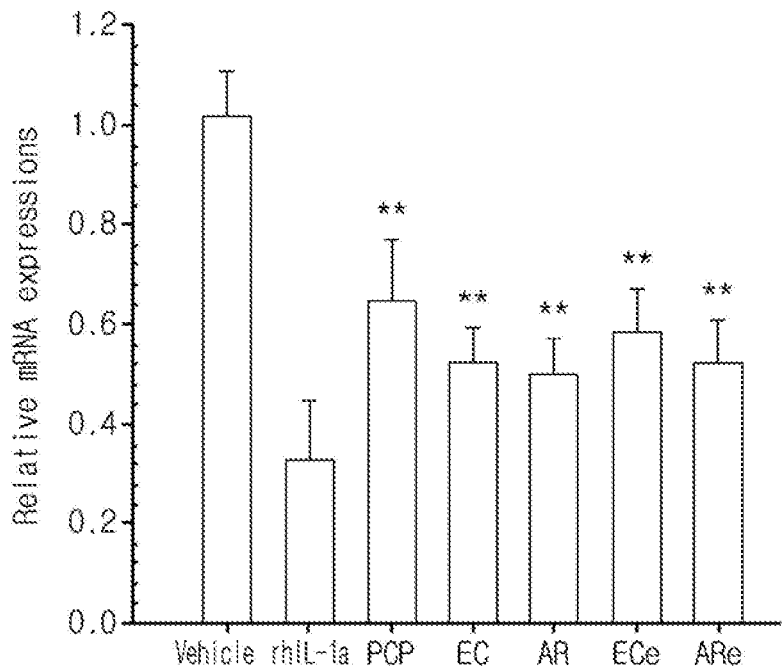
FIG. 5 shows the change in the expression level of collagen type II mRNA depending on treatment with a pomegranate concentrate powder (PCP), a eucommia bark water extract powder (EC), an achyranthis radix water extract powder (AR), a eucommia bark ethanol extract powder (ECe) and an achyranthis radix ethanol extract powder (ARe) (The values are mean±SD for 6 experiments. ** indicates p<0.01 with respect to a rhIL-1α-treated group in the LSD test.).

In osteoarthritis, due to the change and death of cartilage cells, which are important in the maintenance of cartilage homeostasis, as a result of inflammatory response, the production of extracellular matrices such as collagen type II, aggrecan, SOX 9, etc. is decreased and their breakdown is accelerated. As a result, the basic structure of the cartilage is destroyed and the cartilage cannot endure the body weight. Therefore, the activity of collagen type II was measured as a chondrogenesis marker. First, after pretreating the cartilage cells with the test substances at different concentrations for 1 hour, the cartilage cells were treated with rhIL-1α for 2 hours and expression was investigated through RT-PCR. It was confirmed that the rhIL-1α resulted in significantly decreased expression of collagen type II mRNA in the articular cartilage cells isolated from the SD rat. The expression of the collagen type II mRNA associated with the extracellular matrices of the cartilage cells was significantly increased by the pomegranate concentrate powder, the eucommia bark ethanol extract, the achyranthis radix ethanol extract, the eucommia bark water extract and the achyranthis radix water extract in that order. This result suggests that the test substances promote the production of extracellular matrices by cartilage cells and, therefore, are effective in protecting the cartilage tissue (FIG. 5).

2.2. Evaluation of Efficacy Through Animal Experiments

The osteoarthritis-improving effect of the single or mixed formula of the pomegranate concentrate powder (PCP), the eucommia bark water extract powder (EC) and the achyranthis radix water extract powder (AR) was evaluated. As the representative osteoarthritis (OA) experimental animal model, rats with osteoarthritis (OA) induced by anterior cruciate ligament transaction and partial medial meniscectomy were used [Kim et al., 2012; Kang et al., 2014a; Moon et al., 2014; Choi et al., 2015]. From 6 days after the osteoarthritis (OA) surgery, the rats were orally administered with single formulas of PCP, EC and AR and 9 mixed formulas of PCP, EC and AR (200 mg of mixed formula containing PCP (100 mg) and EC:AR (1:1, 1:2, 1:4, 1:6, 1:8, 2:1, 4:1, 6:1 and 8:1, 100 mg) (Table 2) dissolved in sterilized distilled water at a dosage of 5 mL/kg (200 mg/kg) once a day for 28 days. The change in body weight and knee joint thickness was observed for 28 days. On the final day, the PGE2 content, MMP-2 activity and collagen type II mRNA expression in the femoral articular cartilage were analyzed along with the change in knee joint thickness. In addition, the change in articular cartilage thickness and the number of cyclooxygenase (COX)-2- and tumor necrosis factor (TNF)-α-immunopositive cells in the tibial articular cartilage was monitored [Moore et al. 2005; Kim et al., 2012; Kang et al., 2014a; Choi et al., 2015]. Through this experiment, the anti-inflammatory effect and cartilage-regenerating effect of the pomegranate concentrate powder, the eucommia bark extract and the achyranthis radix extract were evaluated.

The mixed formulas exhibiting statistically significant ($p<0.01$ or $p<0.05$) increase in medicinal effect as compared to the each of the single formulas of the pomegranate concentrate powder (PCP), the eucommia bark water extract powder (EC) and the achyranthis radix water extract powder (AR) were regarded as the mixed formulas of the pomegranate concentrate powder, the eucommia bark extract powder and the achyranthis radix extract powder exhibiting a synergistic effect. A group to which 2 mg/kg diclofenac sodium, which is a control drug generally used in osteoarthritis (OA) experiments, was subcutaneously administered was used as a control group [Kim et al., 2012; Kang et al., 2014a; Moon et al., 2014; Choi et al., 2015].

170 healthy SPF/VAF outbred Crl:CD [Sprague-Dawley, SD] male rats (OrientBio, Seungnam, Korea) were accustomed to the laboratory environment for 7 days and subjected to osteoarthritis (OA) or sham surgery. 6 days after the surgery, the rats were divided into 12 groups, with 10 per each group, based on body weight (sham surgery group: 264.40±19.48 g on average, 222-283 g; osteoarthritis (OA)-induced group: 253.98±13.77 g on average, 222-301 g) and knee joint thickness (sham surgery group: 10.00±0.35 mm on average, 9.52-10.57 mm; osteoarthritis (OA)-induced group: 13.44±0.59 mm on average, 12.50-16.38 mm). The animal experiment was conducted under the approval from the Daegu Haany University Animal Care and Use Committee (Table 2).

TABLE 2

| Sample composite ratio | Pomegranate concentrate powder (PCP) (mg) | Eucommia bark extract powder (EC) (mg) | Achyranthis radix extract powder (AR) (mg) |
| --- | --- | --- | --- |
| PCP 100% | 200 | 0 | 0 |
| EC 100% | 0 | 200 | 0 |
| AR 100% | 0 | 0 | 200 |
| 100:50:50 | 100 | 50 | 50 |
| 100:33:67 | 100 | 33 | 67 |
| 100:20:80 | 100 | 20 | 80 |
| 100:14:86 | 100 | 14 | 86 |
| 100:11:89 | 100 | 11 | 89 |
| 100:67:33 | 100 | 67 | 33 |
| 100:80:20 | 100 | 80 | 20 |
| 100:86:14 | 100 | 86 | 14 |
| 100:89:11 | 100 | 89 | 11 |

Composition and Administration of Test Substances:

An adequate amount of PCP, EC or AR was dissolved in sterilized distilled water and orally administered at a dosage of 5 mL/kg from 7 days after the osteoarthritis (OA) surgery once a day for 28 days. That is to say, each of the single formulas of PCP, EC and AR and the mixed formulas of PCP and EC:AR (1:1, 1:2, 1:4, 1:6, 1:8, 2:1, 4:1, 6:1 and 8:1) was orally administered at a dosage of 200 mg/kg for 28 days. For the sham surgery (sham) and osteoarthritis (OA) control groups, only sterilized distilled water was orally administered instead of the test substances. 2 mg of diclofenac sodium (Wako Pure Chemical Ind. Ltd., Osaka, Japan) dissolved in 5 mL of sterilized physiological saline was subcutaneously administered into the back skin at a dosage of 5 mL/kg (2 mg/kg) from 7 days after the osteoarthritis (OA) surgery once a day for 28 days. The administration dosage was set to 2,000 mg/60 kg×6=200 mg/kg, corresponding to 6 times the expected dosage for human (2,000 mg) in consideration of the body surface area of the rat. The dosage of the single formulas of PCP, EC and AR was also set to 200 mg/kg for direct comparison of medicinal effect. The 9 mixed formulas contained PCP corresponding to half (100 mg) of the formula of and EC:AR at ratios of 1:1, 1:2, 1:4, 1:6, 1:8, 2:1, 4:1, 6:1 and 8:1 (50:50, 33:67, 20:80, 14:86, 11:89, 67:33, 80:20, 86:14 and 89:11 (mg:mg)). The mixed formulas were prepared at least once a week by dissolving PCP, EC and AR of adequate amounts at the same time and kept in a refrigerator at 4° C. The single formulas were prepared at least once a week by dissolving 200 mg of PCP, EC or AR in 5 mL of sterilized distilled water and kept in a refrigerator at 4° C.

Induction of Osteoarthritis (OA):

After inducing general inhalation anesthesia of the experimental animal with a mixture gas 2-3% isoflurane (Hana Pharm. Co., Hwaseong, Korea), 70% $N_2O$ and 28.5% $O_2$, the left articular capsule was exposed and osteoarthritis (OA) was induced by anterior cruciate ligament transaction and partial medial meniscectomy while maintaining anesthesia with a mixture gas 1-1.5% isoflurane, 70% $N_2O$ and 28.5% $O_2$. For the sham surgery group, the articular capsule was excised to observe the medial meniscus and then closed without surgical removal.

2.2.1. Osteoarthritis-Improving Effect in Osteoarthritis (OA)-Induced Model

Osteoarthritis (OA) is a representative chronic inflammatory disease. It is known that, in osteoarthritis (OA), as the expression of COX-2 and 5-LPO is increased, PGE2 and leukotriene are produced with the effect from IL-1, TNF-α, etc., leading to cartilage damage and significant increase in joint thickness due to swelling of the nearby joint as well as abnormal bone growth and pain [Sailer et al., 1998; Vane et al., 1998; Bensen et al., 1999; Guo et al., 2006; Hardy et al., 2002; Nam et al., 2014]. In this experiment, only the osteoarthritis (OA)-induced group (13.44±0.59 mm on average, 12.50-16.38 mm) which showed significant increase in knee joint thickness from the sham surgery control group (10.00±0.35 mm on average, 9.52-10.57 mm) 6 days after the osteoarthritis (OA) surgery was used. These experimental animals showed decreased thickness of the femoral and tibial articular cartilage as well as increased number of COX-2 and TNF-α-immunopositive cells. In addition, they showed increased PGE2 content in the thighbone and 5-LPO activity. The inflammatory responses increased due to osteoarthritis (OA) were significantly inhibited by the oral administration of the single formulas of PCP, EC and AR and the 9 mixed formulas of PCP and EC:AR continued for 28 days. In particular, the mixed formulas of PCP and EC:AR (4:1, 2:1 and 1:1) showed significant osteoarthritis-treating effects as compared to the groups administered with the single formulas of PCP, EC and AR in that order. This result suggests that the mixed formulas of PCP and EC:AR (4:1, 2:1 and 1:1) synergistically increase the anti-inflammatory effect of PCP, EC and AR for osteoarthritis (OA). Among them, the mixed formula of PCP and EC:AR (4:1) showed the most superior osteoarthritis-improving effect. The oral administration of the mixed formula of PCP and EC:AR (4:1) at a dosage of 200 mg/kg resulted in an anti-inflammatory effect in rats with surgically-induced osteoarthritis (OA) similar to that of the group to which 2 mg/kg diclofenac sodium was subcutaneously administered.

A. Change in Knee Joint Thickness

Figure 6:
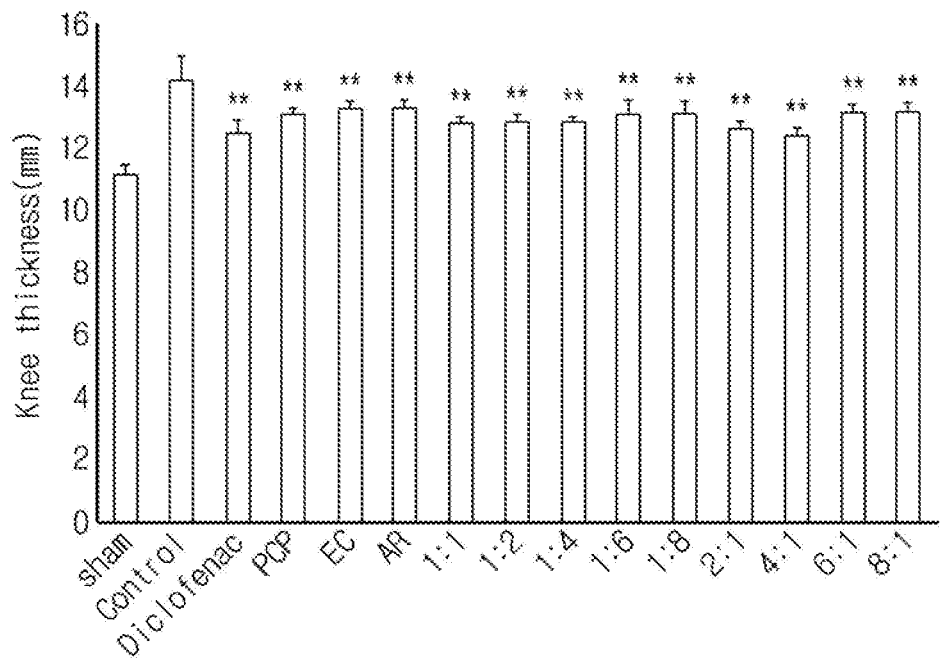
FIG. 6 shows the change in knee joint thickness of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats.).

In this experiment, only the osteoarthritis (OA)-induced group (13.44±0.59 mm on average, 12.50-16.38 mm) which showed significant increase in knee joint thickness from the sham surgery control group (10.00±0.35 mm on average, 9.52-10.57 mm) 6 days after the osteoarthritis (OA) surgery was used. The osteoarthritis (OA) control group showed significant (p<0.01) increase in knee joint thickness as compared to the sham surgery control group throughout the experiment period form 6 days after the osteoarthritis (OA) surgery. The groups administered with diclofenac, the single formula of AR and the mixed formulas of PCP and EC:AR (1:2, 1:8, 2:1 and 4:1) showed significant ($p<0.01$ or $p<0.05$) decrease in knee joint thickness as compared to the osteoarthritis (OA) control group. In particular, the groups administered with the mixed formulas of PCP and EC:AR (2:1 and 4:1) began to show significant ($p<0.01$ or $p<0.05$) decrease in knee joint thickness as compared to the groups treated with the three single formulas from 7 days after the beginning of the administration. From 27 after the beginning of the administration, significant ($p<0.01$ or $p<0.05$) decrease in knee joint thickness was acknowledged as compared to the groups treated with the three single formulas (FIG. 6).

B. Change in PGE2 in Femoral Articular Cartilage

Figure 7:
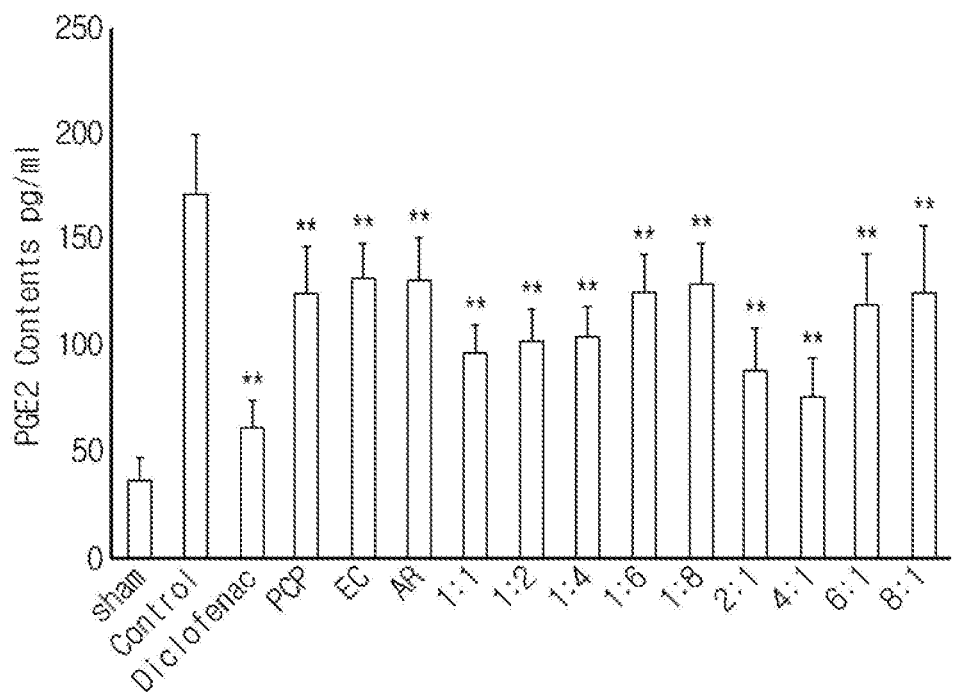
FIG. 7 shows the change in PGE2 content in the femoral articular cartilage of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the MW test. * indicates p<0.05 with respect to an osteoarthritis control group in the MW test.).

The OA control group showed significant ($p<0.01$) increase in the PGE2 in the femoral articular cartilage as compared to the sham surgery control group. All the groups including the group administered with the single formula of AR showed significantly ($p<0.01$ or $p<0.05$) decreased PGE2 content in the femoral articular cartilage as compared to the osteoarthritis (OA) control group. In particular, the groups administered with the mixed formulas of PCP and EC:AR (4:1, 2:1) showed significant ($p<0.01$ or $p<0.05$) decrease in PGE2 content in the femoral articular cartilage as compared to the groups administered with the single formulas of PCP, EC and AR and the groups administered with the mixed formulas of other ratios (FIG. 7).

Figure 8A:
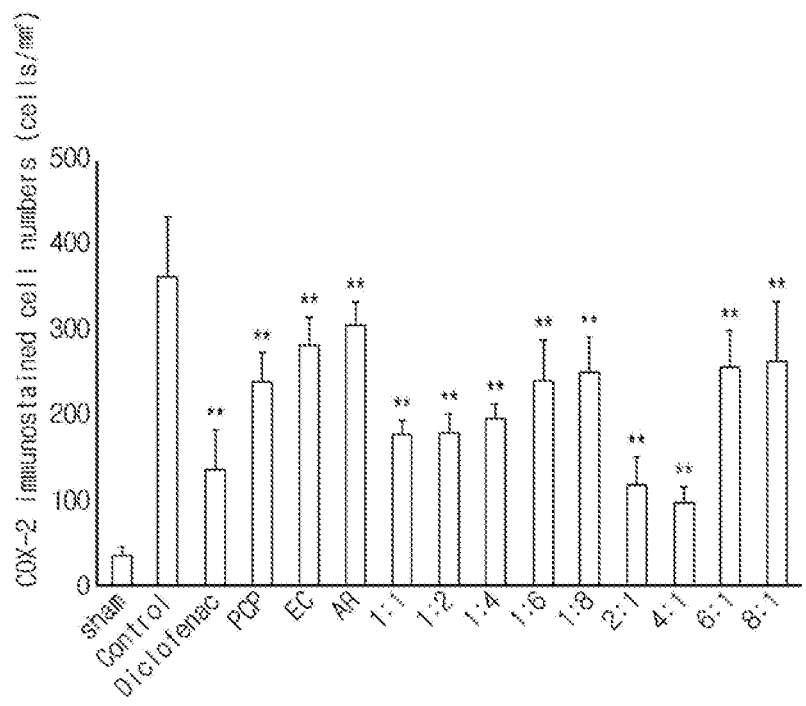
FIGS. 8a and 8b show the change in the number of COX-2-immunopositive cells (FIG. 8a) and TNF-α-immunopositive cells (FIG. 8b) in the femoral and tibial articular cartilage and the joint capsule of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the MW test. * indicates p<0.05 with respect to an osteoarthritis control group in the MW test.).
Figure 8B:
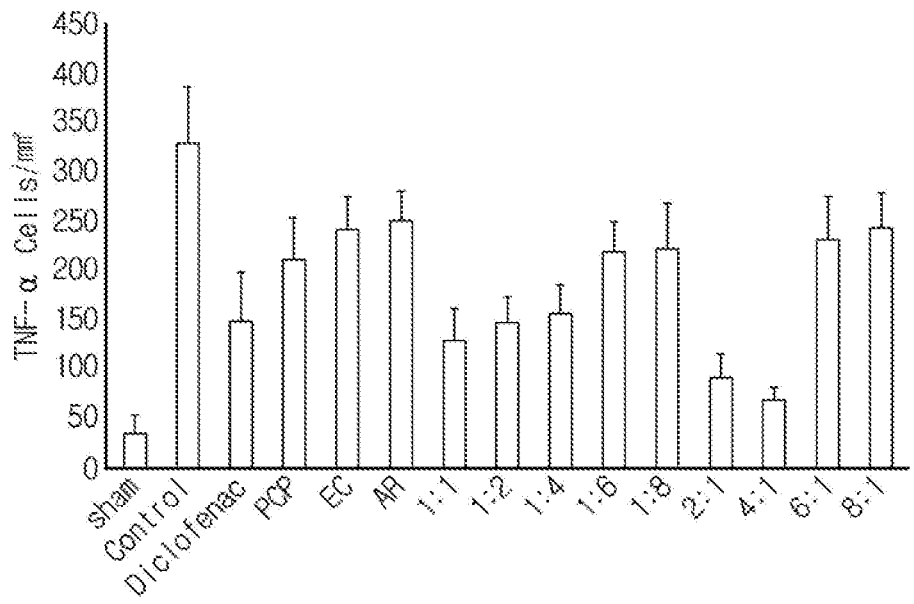

The OA control group showed significant ($p<0.01$) increase in COX-2-immunopositive cells in the femoral articular cartilage as compared to the sham surgery control group. All the groups including the group administered with the single formula of EC showed significant ($p<0.01$ or $p<0.05$) decrease in the number of the COX-2-immunopositive cells in the femoral articular cartilage as compared to the osteoarthritis (OA) control group. In particular, the groups administered with the mixed formulas of PCP and EC:AR (4:1, 2:1) showed significant ($p<0.01$ or $p<0.05$) decrease in the number of the COX-2-immunopositive cells in the femoral articular cartilage as compared to the groups administered with the single formulas of PCP, EC and AR and the groups administered with the mixed formulas of other ratios (FIG. 8).

The OA control group showed significant ($p<0.01$) increase in TNF-α-immunopositive cells in the femoral articular cartilage as compared to the sham surgery control group. All the groups including the group administered with the single formula of AR showed significant ($p<0.01$) decrease in the number of the TNF-α-immunopositive cells in the femoral articular cartilage as compared to the osteoarthritis (OA) control group. In particular, the groups administered with the mixed formulas of PCP and EC:AR (4:1, 2:1) showed significant ($p<0.01$) decrease in the number of the TNF-α-immunopositive cells in the femoral articular cartilage as compared to the groups administered with the single formulas of PCP, EC and AR and the groups administered with the mixed formulas of other ratios (FIG. 8).

2.2.2 Activity of Inhibiting Stiffness

In case of osteoarthritis (OA), the joint movement is very restricted as fibrosis proceeds due to chronic inflammation. Therefore, the maximum stretching angle of the joint is used as a measure of evaluating the joint movement. The smaller the stretching angle, the higher the motility is [Rezende et al., 2006; Kim et al., 2012; Kang et al., 2014a; Moon et al., 2014; Choi et al., 2015].

Figure 9:
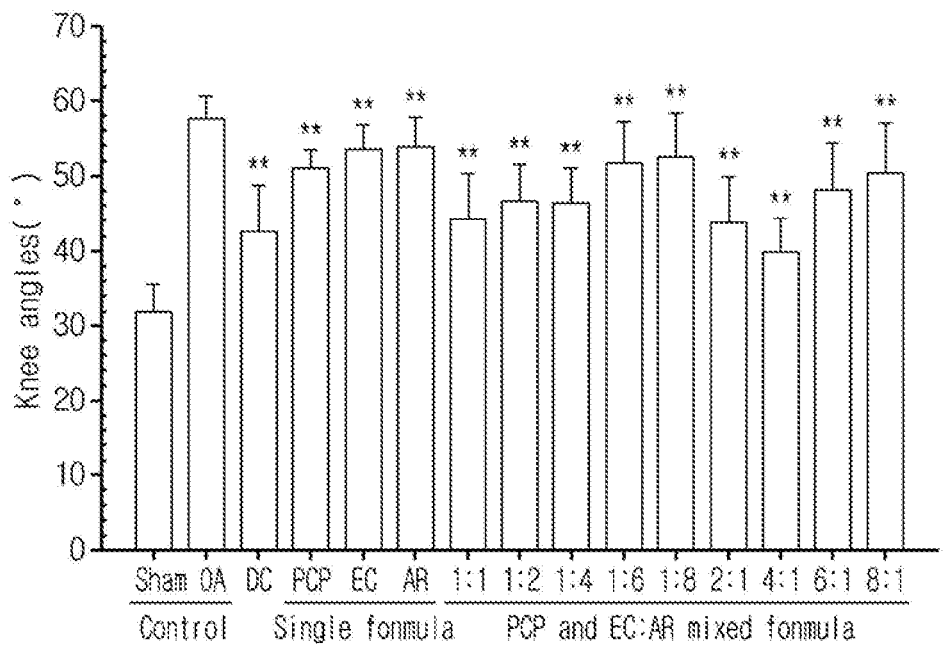
FIG. 9 shows the change in the maximum knee joint stretching angle as a measure of the activity of inhibiting joint stiffness in a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the LDS test. * indicates p<0.05 with respect to an osteoarthritis control group in the LDS test.).

The osteoarthritis (OA) control group showed significant increase in the maximum knee joint stretching angle as compared to the normal control group, which shows that osteoarthritis (OA) was induced relatively well by the surgery. In addition, the thickening of the surface epithelium due to cell proliferation in the joint capsule as a result of joint stiffness due to fibrosis was observed [Permuy et al., 2015ab]. The increased joint stretching angle and the histological thickening of the joint capsule surface epithelium caused by osteoarthritis (OA) were inhibited by the oral administration of the single formulas of PCP, EC and AR and the 9 mixed formulas of PCP and EC:AR for 28 days. In particular, the groups administered with the mixed formulas of PCP and EC:AR (4:1, 2:1) showed decreased significant joint stretching angle and the epithelial thickness of the joint capsule as compared to the groups administered with the single formulas of PCP, EC and AR and the mixed formulas of other ratios. Accordingly, it was confirmed that the mixed formulas of PCP and EC:AR (4:1) exhibit the most superior joint stiffness-inhibiting effect and the oral administration of the mixed formulas of PCP and EC:AR (4:1) at 200 mg/kg exhibit a joint stiffness-inhibiting effect in rats with surgically-induced osteoarthritis (OA) similar to that of the group subcutaneously administered with 2 mg/kg diclofenac (FIG. 9).

2.2.3. Effect of Regenerating and Protecting Cartilage

The extracellular matrix of cartilage mainly consists of collagen and PGs such as glycosaminoglycan and aggrecan [Innes et al., 2013; Qin et al., 2013; Na et al., 2014] and SOX9 is known as a transcription factor essential in the differentiation of cartilage cells [Mundlos and Olsen, 1997]. In osteoarthritis (OA), due to the change and death of cartilage cells, which are important in the maintenance of cartilage homeostasis, as a result of inflammatory response, the production of extracellular matrices such as collagen type II, aggrecan, SOX 9, etc. is decreased and their breakdown is accelerated. As a result, the basic structure of the cartilage is destroyed and the cartilage cannot endure the body weight, resulting in inflammation and pain [Guzman et al., 2003]. Therefore, the inhibition of the loss of the extracellular matrices has been used as one of major targets in treatment of osteoarthritis (OA) [Rai et al., 2011; Innes et al., 2013; Warnock et al., 2014].

The decrease in the expression of the mRNAs of collagen type II, which is a constituent of the cartilage extracellular matrix, was confirmed in the femoral articular cartilage through experiments. The increase in the expression of the mRNAs of collagen type II thought as the cause of articular fibrosis and stiffness caused by s (OA) [Rezende et al., 2006; Kim et al., 2012; Kang et al., 2014a; Moon et al., 2014; Choi et al., 2015] was confirmed in the joint capsule.

The oral administration of the single formulas of PCP, EC and AR and the 9 mixed formulas of PCP and EC:AR inhibited the decrease in the expression of chondrogenesis-related mRNAs. In particular, the groups administered with the mixed formulas of PCP and EC:AR (4:1, 2:1) significantly inhibited the decrease in the expression of chondrogenesis-related mRNAs as compared to the groups administered with the single formulas of PCP, EC and AR or mixed formulas of other ratios. The oral administration of the mixed formula of PCP and EC:AR (4:1) at 200 mg/kg exhibited an effect of inhibiting the change in the expression of chondrogenesis-related mRNAs in rats with surgically-induced osteoarthritis (OA) similar to that of the group subcutaneously administered with 2 mg/kg diclofenac. Accordingly, it is thought that the mixed formulas of PCP and EC:AR of adequate ratios synergistically enhance the cartilage extracellular matrix formation and anti-fibrosis effects in the joint capsule through anti-inflammation and protection and promoted proliferation of cartilage cells. Among them, the mixed formula of PCP and EC:AR (4:1)

showed the most superior effect of promoting cartilage extracellular matrix formation. The increased expression of collagen type II, SOX9 and aggrecan mRNAs in the femoral and tibial articular cartilage observed in the group subcutaneously administered with diclofenac is thought as a secondary effect resulting from the anti-inflammation and protection and promoted proliferation of cartilage cells by diclofenac because the increase in the number of BrdU-immunopositive cells was not observed.

A. Change in Expression of Collagen Type II mRNA in Femoral Articular Cartilage

The OA control group showed significant ($p<0.01$) decrease in collagen type II mRNA expression in the femoral and tibial articular cartilage as well as significant ($p<0.01$) increase in collagen type II mRNA expression in the joint capsule as compared to the sham surgery control group.

All the groups including the groups administered with single formulas showed significant ($p<0.01$ or $p<0.05$) increase in collagen type II mRNA expression in the femoral and tibial articular cartilage and decrease in collagen type II mRNA expression in the joint capsule as compared to the osteoarthritis (OA) control group. In particular, the groups administered with the mixed formulas of PCP and EC:AR (4:1, 2:1) showed significant ($p<0.01$ or $p<0.05$) increase in collagen type II mRNA expression in the femoral and tibial articular cartilage and decrease in collagen type II mRNA expression in the joint capsule as compared to the groups administered with the single formulas of PCP, EC and AR and the groups administered with the mixed formulas of other ratios (Table 3).

TABLE 3

| Groups | Items Collagen type II mRNA expressions | | |
|---|---|---|---|
| | Femur AC | Tibia AC | SM |
| Controls | | | |
| Sham | 1.05 ± 0.16 | 1.01 ± 0.12 | 1.01 ± 0.21 |
| OA | 0.34 ± 0.11$^a$ | 0.31 ± 0.07$^i$ | 5.41 ± 1.27$^i$ |
| Diclofenac | 0.69 ± 0.10$^{ab}$ | 0.64 ± 0.11$^{ij}$ | 2.74 ± 0.95$^{ij}$ |
| Single formula | | | |
| PCP | 0.51 ± 0.10$^{ab}$ | 0.49 ± 0.04$^{ij}$ | 3.73 ± 0.35$^{ij}$ |
| EC | 0.49 ± 0.10$^{ab}$ | 0.44 ± 0.07$^{ij}$ | 4.05 ± 0.50$^{ij}$ |
| AR | 0.46 ± 0.06$^{ac}$ | 0.40 ± 0.06$^{ij}$ | 4.04 ± 0.47$^{ij}$ |
| Mixed formula - PCP and EC:AR | | | |
| 1:1 | 0.62 ± 0.06$^{abefn}$ | 0.62 ± 0.09$^{ijlno}$ | 2.79 ± 0.54$^{ijlno}$ |
| 1:2 | 0.61 ± 0.07$^{abegn}$ | 0.58 ± 0.07$^{ijlno}$ | 3.04 ± 0.48$^{ijlno}$ |
| 1:4 | 0.61 ± 0.08$^{abefn}$ | 0.56 ± 0.05$^{ijlno}$ | 3.12 ± 0.48$^{ijmno}$ |
| 1:6 | 0.52 ± 0.10$^{ab}$ | 0.47 ± 0.11$^{ij}$ | 3.87 ± 1.00$^{ik}$ |
| 1:8 | 0.49 ± 0.11$^{ab}$ | 0.46 ± 0.09$^{ij}$ | 3.96 ± 0.83$^{ij}$ |
| 2:1 | 0.66 ± 0.10$^{abdfn}$ | 0.66 ± 0.11$^{ijlno}$ | 2.35 ± 0.61$^{ijlno}$ |
| 4:1 | 0.71 ± 0.11$^{abdfn}$ | 0.70 ± 0.14$^{ijlno}$ | 1.98 ± 0.51$^{ijlno}$ |
| 6:1 | 0.52 ± 0.12$^{ab}$ | 0.49 ± 0.14$^{ij}$ | 3.88 ± 0.85$^{ij}$ |
| 8:1 | 0.50 ± 0.08$^{ab}$ | 0.44 ± 0.10$^{ij}$ | 3.97 ± 0.95$^{ik}$ |

B. Change in Femoral Articular Cartilage Thickness

In osteoarthritis (OA), the articular cartilage thickness is significantly decreased due to articular cartilage damage [Moore et al., 2005; Patel et al., 2005; Cao et al., 2006; Kim et al., 2012; Kang et al., 2014a; Moon et al., 2014; Choi et al., 2015].

Figure 10:
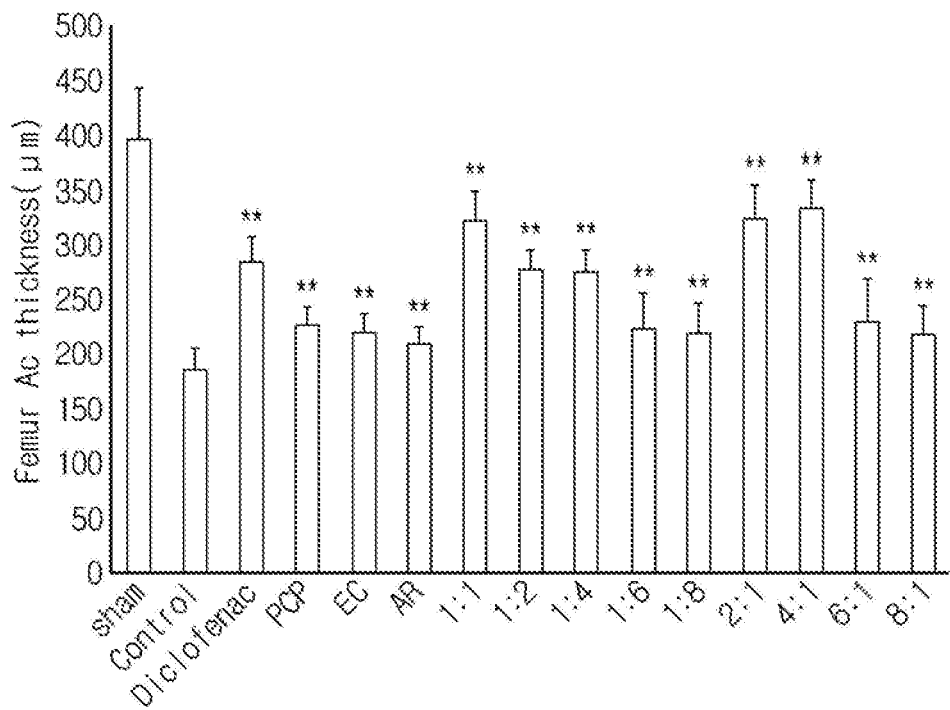
FIG. 10 shows the change in the femoral articular cartilage thickness of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the LDS test. * indicates p<0.05 with respect to an osteoarthritis control group in the LDS test.).

The oral administration of the single formulas of PCP, EC and AR and the 9 mixed formulas of PCP and EC:AR for 28 days inhibited the decrease in tibial articular cartilage thickness. In particular, the groups administered with the mixed formulas of PCP and EC:AR (4:1, 2:1, 1:1) showed significant increase in the femoral articular cartilage thickness capsule as compared to the groups administered with the single formulas of PCP, EC and AR and the groups administered with the mixed formulas of other ratios. Accordingly, it was confirmed that the mixed formula of PCP and EC:AR (4:1) exhibits the most superior articular cartilage-protecting effect (FIG. 10).

C. Change in Cell Proliferation in Femoral Articular Cartilage—Change in BrdU-Immunopositive Cells Detection based on BrdU uptake using primary antibodies is a method commonly used to investigate cell proliferation [Ganey et al., 2003; Moore et al., 2005; Kim et al., 2012; Kang et al., 2014a; Moon et al., 2014; Choi et al., 2015]. The cells containing the injected BrdU are those that have proliferated newly or are proliferating actively.

Figure 11:
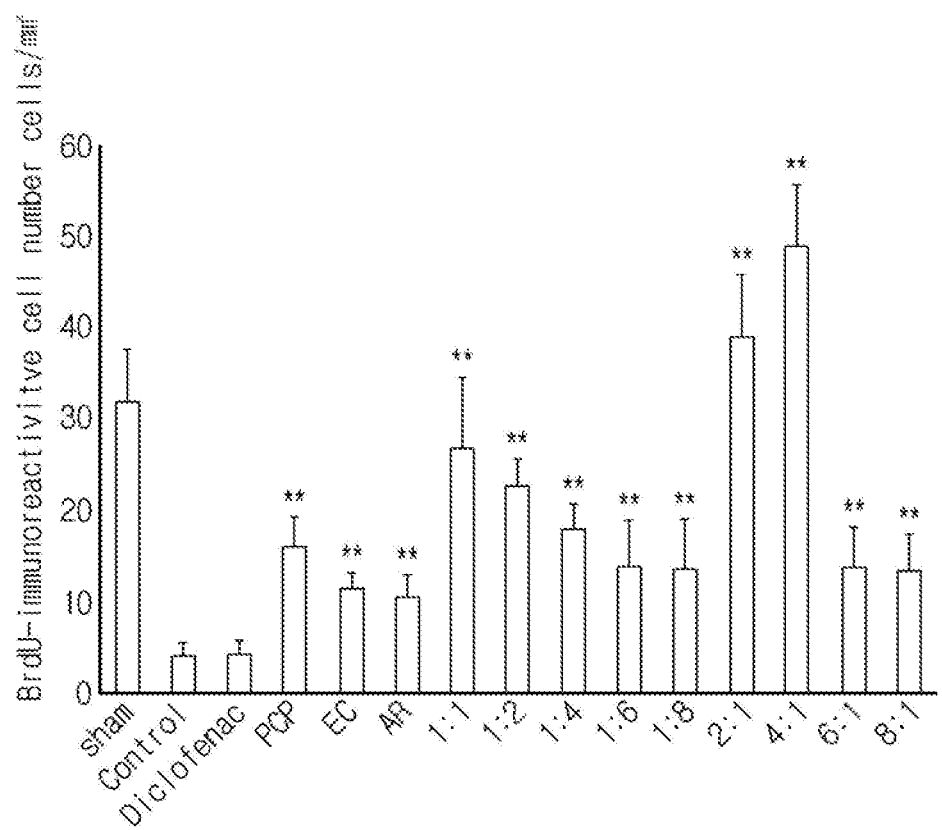
FIG. 11 shows the change in the number of BrdU-immunopositive cells as a measure of the change in cell proliferation in the femoral articular cartilage of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the MW test. * indicates p<0.05 with respect to an osteoarthritis control group in the MW test.).

The osteoarthritis (OA) control group showed significant decrease in the number of BrdU-immunopositive cells in the femoral and tibial articular cartilage and decrease in the number of BrdU-immunopositive cells, indicative of inflammatory cell infiltration and proliferative fibrosis, in the joint capsule as compared to the sham surgery control group. The diclofenac-administered group showed decrease in the number of BrdU-immunopositive cells in the joint capsule, indicative of the anti-inflammatory effect, as compared to the osteoarthritis (OA) control group, but showed similar change in the number of BrdU-immunopositive cells in the femoral and tibial articular cartilage as the osteoarthritis (OA) control group. The groups administered with the single formulas of PCP, EC and AR and the 9 mixed formulas of PCP and EC:AR showed significant increase in the number of BrdU-immunopositive cells in the femoral and tibial articular cartilage, indicative of the proliferation of cartilage cells, and decrease in the number of BrdU-immunopositive cells in the joint capsule, indicative of the anti-inflammatory effect, as compared to the osteoarthritis (OA) control group. In particular, the groups administered with the mixed formulas of PCP and EC:AR (4:1, 2:1) showed significant increase in the number of BrdU-immunopositive cells in the femoral and tibial articular cartilage and decrease in the number of BrdU-immunopositive cells in the joint capsule as compared to the groups administered with the single formulas of PCP, EC and AR and the mixed formulas of other ratios. It was confirmed that the mixed formula of PCP and EC:AR (4:1) showed the most superior effect of promoting the proliferation of articular cartilage cells (FIG. 11).

D. Change in MMP-2 and MMP-9 Activity in Femoral Articular Cartilage

In the inflammatory joint, protein-degrading enzymes such as MMP play an important role in cartilage and bone destruction. MMP is inhibited by the antagonistic system in tissues [Bresnihan, 1999]. In addition, because MMP acts as an extracellular matrix protein in vivo and is involved in the degradation of PG in osteoarthritis [Nagasa and Woessner, 1999], the regulation of MMP activity is known to be very important in the treatment of arthritis [Halliwell, 2000; Na et al., 2014].

The osteoarthritis (OA) control group showed increased MMP-2 and MMP-9 activity in the femoral articular cartilage. The oral administration of the single formulas of PCP, EC and AR and the 9 mixed formulas of PCP and EC:AR for 28 days inhibited the increase in MMP-2 and MMP-9 activity. In particular, the groups administered with the mixed formulas of PCP and EC:AR (4:1, 2:1) showed significant decrease in MMP-2 and MMP-9 activity in the femoral articular cartilage as compared to the groups administered with the single formulas of PCP, EC and AR and the mixed formulas of other ratios.

Figure 12A:
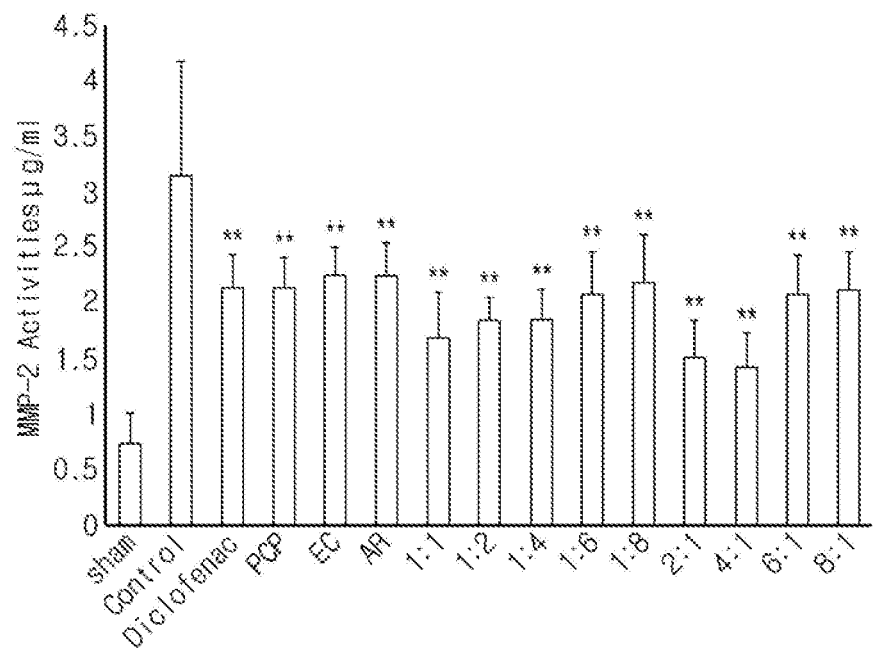
FIG. 12 shows the change in the activity of MMP-2 and MMP-9 in the femoral articular cartilage of a surgically induced osteoarthritis rat model depending on treatment with a pomegranate concentrate powder (PCP), a eucommia bark water extract powder (EC) and an achyranthis radix water extract powder (AR) either alone or in combination (The values are mean±SD for 10 rats. ** indicates p<0.01 with respect to an osteoarthritis control group in the MW test. * indicates p<0.05 with respect to an osteoarthritis control group in the MW test.).
Figure 12B:
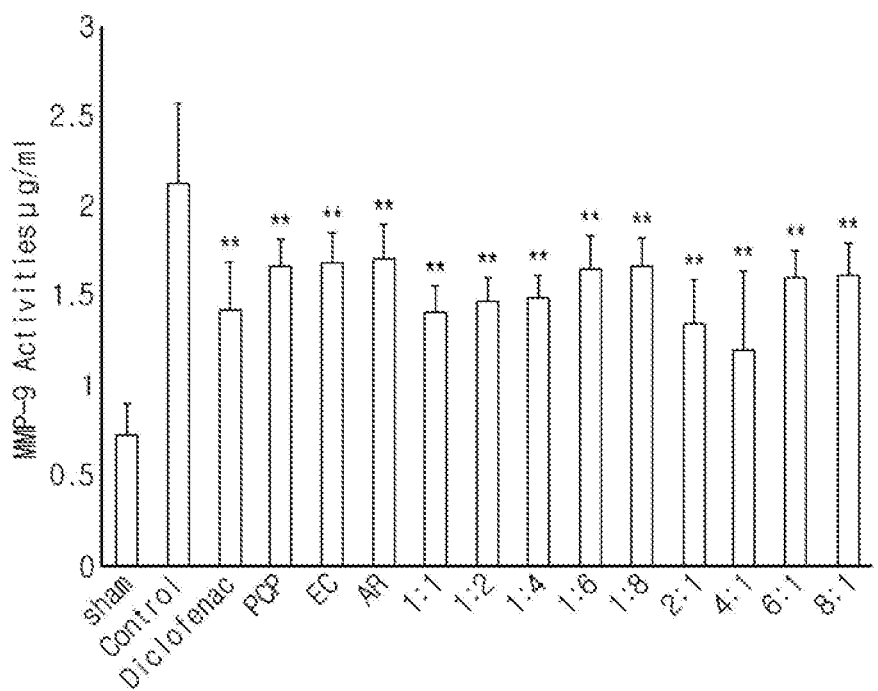

Accordingly, it is though that the mixed formulas of PCP and EC:AR (4:1, 2:1) synergistically enhances the cartilage cell-protecting effect of PCP, EC and AR through inhibition of MMP activity. Among them, the mixed formula of PCP and EC:AR (4:1) showed the most superior effect of inhibiting MMP-2 and MMP-9 activity. The oral administration of the mixed formula of PCP and EC:AR (4:1) at 200 mg/kg inhibited MMP-2 and MMP-9 activity in rats with surgically-induced osteoarthritis (OA) similarly to the group subcutaneously administered with 2 mg/kg diclofenac (FIG. 12).

E. Confirmation of Osteoarthritis-Improving Effect for Osteoarthritic Subjects Using Western Ontario and McMaster Universities Arthritis Index (WOMAC)

In order to confirm the osteoarthritis-improving effect, mixed formulas of achyranthis radix, eucommia bark, pomegranate, etc. were administered to Korean subjects suffering from osteoarthritis at dosages of 500 mg/day or 1000 mg/day for 12 weeks. The effect was evaluated based on joint pain, joint stiffness and inconvenience in daily lives. The mixed formulas showed significant improvement in joint pain, joint stiffness and inconvenience in daily lives.

What is claimed is:

1. A method of treating a subject having osteoarthritis, comprising administering a composition comprising therapeutically effective amounts of a pomegranate concentrate, a Eucommia bark extract and an Achyranthis radix extract as active ingredients to the subject.

2. The method according to claim 1, wherein a weight ratio of the Eucommia bark extract to the Achyranthis radix extract is 2:1-41.

3. The method according to claim 1, wherein a weight ratio of the pomegranate concentrate to the Eucommia bark extract to the Achyranthis radix extract is 5:2:1-5:4:1.

4. The method according to claim 1, wherein the pomegranate concentrate is obtained by treating a pomegranate pulp with a starch-degrading enzyme and then concentrating under heating.

5. The method according to claim 1, wherein an extraction solvent of the Eucommia bark extract or the Achyranthis radix extract is water, a C1-C4 alcohol or a mixture thereof.

6. The method according to claim 1, wherein the pomegranate concentrate comprises 0.5-2 mg/g of ellagic acid.

7. The according to claim 1, wherein the Eucommia bark extract is an Eucommia bark water extract comprising 0.5-3 mg/g of pinoresinol diglucoside.

8. The method according to claim 1, wherein the Eucommia bark extract is an Eucommia bark alcohol extract comprising 0.8-4 mg/g of pinoresinol diglucoside.

9. The method according to claim 1, wherein the Achyranthis radix extract is an Achyranthis radix water extract comprising 0.1-0.5 mg/g of ecdysterone.

10. The method according to claim 1, wherein the Achyranthis radix extract is an Achyranthis radix alcohol extract comprising 0.2-2.5 mg/g of ecdysterone.

11. The method according to claim 1, wherein the composition has an effect of protecting cartilage, regenerating cartilage or improving joint stiffness.

12. The method according to claim 1, wherein the composition is a health functional food composition or a pharmaceutical composition.

* * * * *